(12) United States Patent
Zheng

(10) Patent No.: US 8,716,243 B2
(45) Date of Patent: May 6, 2014

(54) METHODS OF EFFECTING WNT SIGNALING THROUGH DKK STRUCTURAL ANALYSIS

(75) Inventor: Jie Zheng, Memphis, TN (US)

(73) Assignee: St. Jude Childen's Research Hospital, Memphis, TN (US)

( * ) Notice: Subject to any disclaimer, the term of this patent is extended or adjusted under 35 U.S.C. 154(b) by 751 days.

(21) Appl. No.: 12/454,758

(22) Filed: May 22, 2009

(65) Prior Publication Data

US 2009/0312253 A1 Dec. 17, 2009

Related U.S. Application Data

(60) Provisional application No. 61/130,098, filed on May 28, 2008.

(51) Int. Cl.
| | | |
|---|---|---|
| A61K 38/16 | (2006.01) | |
| A61K 38/00 | (2006.01) | |
| A61P 19/08 | (2006.01) | |
| A61P 19/10 | (2006.01) | |

(52) U.S. Cl.
USPC ....... 514/21.2; 514/16.6; 514/16.7; 514/16.9; 514/17.8; 514/19.2; 435/377

(58) Field of Classification Search
None
See application file for complete search history.

(56) References Cited

U.S. PATENT DOCUMENTS

| | | | |
|---|---|---|---|
| 6,344,541 B1 * | 2/2002 | Bass et al. | 530/324 |
| 2004/0014209 A1 * | 1/2004 | Lassar et al. | 435/366 |
| 2005/0070699 A1 * | 3/2005 | Allen et al. | 536/23.2 |
| 2005/0196349 A1 | 9/2005 | Wu et al. | |
| 2006/0030523 A1 | 2/2006 | Wu et al. | |
| 2008/0119402 A1 | 5/2008 | Zheng et al. | |
| 2010/0041599 A1 | 2/2010 | Liu et al. | |
| 2010/0298200 A1 | 11/2010 | Liu et al. | |
| 2010/0298308 A1 | 11/2010 | Wu et al. | |
| 2011/0105606 A1 | 5/2011 | Rabbani et al. | |

OTHER PUBLICATIONS

Mao et al., Nature. May 17, 2001;411(6835):321-325.*
Bafico, A., Liu, G., Yaniv, A., Gazit, A., and Aaronson, S. A., Novel mechanism of Wnt signaling inhibition mediated by Dickkopf-1 interaction with LRP6/Arrow, Nat. Cell Biol. 2001, 683-686, 3.
Boisbouvier, J., Albrand, J. P., Blackledge, M., Jaquinod, M., Schweitz, H., Lazdunski, M., and Marion, D., A structural homologue of colipase in black mamba venom revealed by NMR floating disulphide bridge analysis, J. Mol. Biol. 1998, 205-219, 283.
Bonvin, A. M. , Flexible protein-protein docking, Curr. Opin. Struct. Biol. 2006, 194-200,16.
Brott, B. K., and Sokol, S. Y., Regulation of Wnt/LRP signaling by distinct domains of Dickkopf proteins, Mol. Cell. Biol. 2002, 6100-6110, 22.
Case, D. A., Cheatham, T. E., III, Darden, T., Gohlke, H., Luo, R., Merz, K. M., Jr., Onufriev, A., Simmerling, C., Wang, B., and Woods, R. J., The amber biomolecular simulation programs, J. Comput. Chem. 2005, 1668-1688, 26.
Delaglio, F., Grzesiek, S., Vuister, G. W., Zhu, G., Pfeifer, J., and Bax, A., NMR pipe: a multidimensional spectral processing system based on UNIX pipes, J. Biomol. NMR, 1995, 277-293, 6.
DeVries, S. J., Van Dijk, A. D., Krzeminski, M., Van, D. M., Thureau, A., Hsu, V., Wassenaar, T., and Bonvin, A. M., Haddock versus Haddock: new features and performance of Haddock 2.0 on the Capri targets, Proteins 2007, 726-733, 69.
Dominguez, C., Boelens, R., and Bonvin, A. M., Haddock: a protein-protein docking approach based on biochemical or biophysical information, J. Am. Chem. Soc. 2003, 1731-1737, 125.
Eccles, C., Guntert, P., Billeter, M., and Wuthrich, K., Efficient analysis of protein 2D NMR spectra using the software package EASY, J. Biomol. NMR 1991, 111-130, 1.
Esnouf, R. M., An extensively modified version of Molscript that includes greatly enhanced coloring capabilities, J. Mol. Graph. Model. 1997, 132-134, 15.
Gray, J. J. , High-resolution protein-protein docking, Curr. Opin. Struct. Biol. 2006, 183-193, 16.
Guntert, P., Braun, W., and Wuthrich, K., Efficient computation of three-dimensional protein structures in solution from nuclear magnetic resonance data using the program Diana and the supporting programs Caliba, Habas and Glomsa, J. Mol. Biol. 1991, 517-530, 217.
Guntert, P., Mumenthaler, C., and Wuthrich, K., Torsion angle dynamics for NMR structure calculation with the new program Dyana, J. Mol. Biol. 1997, 283-298, 273.
Holm, L., and Sander, C., Protein structure comparison by alignment of distance matrices, J. Mol. Biol. 1993, 123-138, 233.
Jeon, H., Meng, W. Y., Takagi, J., Eck, M. J., Springer, T. A., and Blacklow, S. C., Implications for familial hypercholesterolemia from the structure of the LDL receptor YWTD-EGF domain pair, Nat. Struct. Biol. 2001, 499-504, 8.
Koradi, R., Billeter, M., and Wuthrich, K., Molmol: a program for display and analysis of macromolecular structures, J. Mol. Graph. 1996, 29-32, 14.
Krupnik, V. E., Sharp, J. D., Jiang, C., Robison, K., Chickering, T. W., Amaravadi, L., Brown, D. E., Guyot, D., Mays, G., Leiby, K., Chang, B., Duong, T., Goodearl, A. D., Gearing, D. P., Sokol, S. Y., and McCarthy, S. A., Functional and structural diversity of the human dickkopf gene family, Gene 1999, 301-313, 238.
Li, L., Mao, J. H., Sun, L., Liu, W. Z., and Wu, D. Q., Second cysteine-rich domain of Dickkopf-2 activates canonical Wnt signaling pathway via LRP-6 independently of dishevelled, J. Biol. Chem. 2002, 5977-5981, 277.
Li, L., Yuan, H., Xie, W., Mao, J., Caruso, A. M., McMahon, A., Sussman, D. J., and Wu, D., Dishevelled proteins lead to two signaling pathways, J. Biol. Chem.1999, 129-134, 274.

(Continued)

*Primary Examiner* — Daniel C Gamett
(74) *Attorney, Agent, or Firm* — Anna D. Digabriele Petti, Esq.

(57) ABSTRACT

Compositions and methods related to Wnt signaling regulation by Dickkopf (Dkk) polypeptides and Wnt-related diseases are disclosed. For example, compounds that bind a Dkk or LRP polypeptide are disclosed. Compounds that disrupt binding of a Dkk polypeptide to an LRP polypeptide are also disclosed. Methods for using the described compounds and compositions are also disclosed.

13 Claims, 6 Drawing Sheets

(56) References Cited

OTHER PUBLICATIONS

Li, Y., Lu, W., He, X., Schwartz, A. L., and Bu, G., LRP6 expression promotes cancer cell proliferation and tumorgenesis by altering beta-catenin subcellular distribution, Oncogene 2004, 9129-9135, 23.

Mao, B., and Niehrs, C., Kremen2 modulates Dickkopf2 activity during Wnt/LRP6 signaling, Gene 2003, 179-183, 302.

Mao, B., Wu, W., Davidson, G., Marhold, J., Li, M., Mechler, B. M., Delius, H., Hoppe, D., Stannek, P., Walter, C., Glinka, A., and Niehrs, C., Kremen proteins are Dickkopf receptors that regulate Wnt/beta-catenin signaling, Nature 2002, 664-667, 417.

Mendez, R., Leplae, R., Lensink, M. F., and Wodak, S. J., Assessment of Capri prediction in rounds 3-5 shows progress in docking procedures, Proteins 2005, 150-169, 60.

Niehrs, C., Function and biological roles of the Dickkopf family of Wnt modulators, Oncogene 2006, 7469-7481, 25.

Rudenko, G., Henry, L., Henderson, K., Ichtchenko, K., Brown, M. S., Goldstein, J. L., and Deisenhofer, Structure of the LDL receptor extracellular domain at endosomal pH, J., Science 2002, 2353-2358, 298.

Sali, A., and Overington, J. P., Derivation of rules for comparative protein modeling from a database of protein structure alignments, Protein Sci. 1994, 1582-1596, 3.

Semenov, M. V., Tamai, K., Brott, B. K., Kuhl, M., Sokol, S., and He, X., Head inducer Dickkopf-1 is a ligand for Wnt coreceptor LRP6, Curr. Biol. 2001, 951-961, 11.

Springer, T. A., An extracellular beta-propeller module predicted in lipoprotein and scavenger receptors, tyrosine kinases, epidermal growth factor precursor, and extracellular matrix components, J. Mol. Biol. 1998, 837-862, 283.

Springer, T. A., Predicted and experimental structures of integrins and beta-propellers, Curr. Opin. Struct. Biol. 2002, 802-813, 12.

Springer, T. A., Folding of the N-terminal, ligand-binding region of integrin alpha-subunits into a beta-propeller domain, Proc. Natl. Acad. Sci. U. S. A. 1997, 65-72, 94.

Takagi, J., Yang, Y., Liu, J. H., Wang, J. H., and Springer, T. A., Complex between nidogen and laminin fragments reveals a paradigmatic beta-propeller interface, Nature 2003, 969-974, 424.

Thornton, J. M., Disulfide bridges in globular proteins, J. Mol. Biol. 1981, 261-287, 151.

Van Dijk, A. D., Boelens, R., and Bonvin, A. M., Data-driven docking for the study of biomolecular complexes, FEBS J. 2005, 293-312, 272.

Van Dijk, M., Van Dijk, A. D., Hsu, V., Boelens, R., and Bonvin, A. M., Information-driven protein-DNA docking using HADDOCK: it is a matter of flexibility, Nucleic Acids Res. 2006, 3317-3325, 34.

Van Tilbeurgh, H., Sarda, L., Verger, R., and Cambillau, C., Structure of the pancreatic lipase-procolipase complex, Nature 1992, 159-162, 359.

Van Tilbeurgh H., Bezzine, S., Cambillau, C., Verger, R., and Carriere, F., Colipase: structure and interaction with pancreatic lipase, Biochim. Biophys. Acta 1999, 173-184, 1441.

Wang, K., Zhang, Y., Li, X., Chen, L., Wang, H., Wu, J., Zheng, J., and Wu, D., Characterization of the Kremen-binding site on DKK1 and elucidation of the role of Kremen in Dkk-mediated Wnt antagonism, J. Biol. Chem. 2008, 23371-23375, 283.

Wong, H. C., Mao, J., Nguyen, J. T., Srinivas, S., Zhang, W., Liu, B., Li, L., Wu, D., and Zheng, Structural basis of the recognition of the dishevelled DEP domain in the Wnt signaling pathway, J. Nat. Struct. Biol. 2000, 1178-1184, 7.

Wong, H. C., Bourdelas, A., Krauss, A., Lee, H.-J., Shao, Y.-M., Wu, D., Mlodzik, M., Shi, D. L., and Zheng, Direct binding of the PDZ domain of dishevelled to a conserved internal sequence in the C-terminal region of frizzled, J. Mol. Cell 2003, 1251-1260, 12.

Wong, H. C., Liu, G., Zhang, Y. M., Rock, C. O., and Zheng, J., The solution structure of acyl carrier protein from *Mycobacterium tuberculosis*, J. Biol. Chem. 2002, 15874-15880, 277.

Zhang, Y., Wang, Y., Li, X., Zhang, J., Mao, J., Li, Z., Zheng, J., Li, L., Harris, S., and Wu, D., The LRP5 high-bone-mass G171V mutation disrupts LRP5 interaction with Mesd, Mol. Cell. Biol. 2004, 4677-4684, 24.

\* cited by examiner

FIGURE 6

| Blade | | | β2 | β3 | β4 | β1 |
|---|---|---|---|---|---|---|
| 6 | hLDLR | 377 | -IAYLFFTNR---HEVRKMTL-----DR-SEYISLIPN- | | | -LRNVVALDTEVA |
| | mNidogen | 913 | -GTHLLFAQT---GKIERLPLERNTMKK-TEAKAFLHI- | | | PAKVIIGLAFDCV |
| | hLRP53 | 643 | PEAFLVFTSR---AAIHRISL---ETNN-NDVAIPLTG- | | | -VKEASALDFDVS |
| | hLRP63 | 630 | PEAFLLFSRR---ADIRRISL---ETNN-NNVAIPLTG- | | | -VKEASALDFDVT |
| | hLRP52 | 340 | AEEVLLLARR---TDLRRISL---DTPDFTDIVLQVDD- | | | -IRHAIAIDYDPL |
| | hLRP62 | 327 | ATELLLLARR---TDLRRISL---DTPDFTDIVLQLED- | | | -IRHAIAIDYDPV |
| | hLRP51 | 31 | ASPLLLFANR---RDVRLVDA---GGVK-LESTIVVSG- | | | -LEDAAAVDFQFS |
| | hLRP61 | 19 | AAPLLLYANR---RDLRLVDA---TNGK-ENATIVVGG- | | | -LEDAAAVDFVFS |
| 1 | hLDLR | 417 | SNRIYWSDLS--QRMICSTQLDRA-HGVSSYDTVISR-- | | | DIQAPDGLAVDWI |
| | mNidogen | 959 | DKVVYWTDIS--EPSIGRASLH-----GGEPTTIIRQ-- | | | DLGSPEGIALDHL |
| | hLRP53 | 686 | NNHIYWTDVS--LKTISRAFMN-----GSSVEHVVEF-- | | | GLDYPEGMAVDWM |
| | hLRP63 | 673 | DNRIYWTDIS--LKTISRAFMN-----GSALEHVVEF-- | | | GLDYPEGMAVDWL |
| | hLRP52 | 384 | EGYVYWTDDE--VRAIRRAYLD-----GSGAQTLVNT-- | | | EINDPDGIAVDWV |
| | hLRP62 | 371 | EGYIYWTDDE--VRAIRRSFID-----GSGSQFVVTA-- | | | QIAHPDGIAVDWV |
| | hLRP51 | 74 | KGAVYWTDVS--EEAIKQTYLNQ---TGAAVQNVVIS-- | | | GLVSPDGLACDWV |
| | hLRP61 | 62 | HGLIYWSDVS--EEAIKRTEFNK---TE-SVQNVVVS-- | | | GLLSPDGLACDWL |
| 2 | hLDLR | 464 | HSNIYWTDSV--LGTVSVADT-----KGVKRKTLFRE-- | | | NGSKPRAIVVDPV |
| | mNidogen | 1002 | GRTIFWTDSQ--LDRIEVAKM-----DGTQRRVLFDT-- | | | GLVNPRGIVTDPV |
| | hLRP53 | 729 | GKNLYWADTG--TNRIEVARL-----DGQFRQVLVWR-- | | | DLDNPRSLALDPT |
| | hLRP63 | 716 | GKNLYWADTG--TNRIEVSKL-----DGQHRQVLVWK-- | | | DLDSPRALALDPA |
| | hLRP52 | 427 | ARNLYWTDTG--TDRIEVTRL-----NGTSRKILVSE-- | | | DLDEPRAIALHPV |
| | hLRP62 | 414 | ARNLYWTDTG--TDRIEVTRL-----NGTMRKILISE-- | | | DLEEPRAIVLDPM |
| | hLRP51 | 119 | GKKLYWTDSE--TNRIEVANL-----NGTSRKVLFWQ-- | | | DLDQPRAIALDPA |
| | hLRP61 | 106 | GEKLYWTDSE--TNRIEVSNL-----DGSLRKVLFWQ-- | | | ELDQPRAIALDPS |
| 3 | hLDLR | 507 | HGFMYWTDWG-TPAKIKKGGL-----NGVDIYSLVTE-- | | | NIQWPNGITLDLL |
| | mNidogen | 1045 | RGNLYWTDWNRDNPKIETSHM-----DGTNRRILAQD-- | | | NLGLPNGLTFDAF |
| | hLRP53 | 772 | KGYIYWTEWG-GKPRIVRAFM-----DGTNCMTLVD--- | | | KVGRANDLTIDYA |
| | hLRP63 | 759 | EGFMYWTEWG-GKPKIECANL-----DGSERTILVP--- | | | NVGRANGLTIDYA |
| | hLRP52 | 470 | MGLMYWTDWG-ENPKIECANL-----DGQERRVLVNA-- | | | SLGWPNGLALDLQ |
| | hLRP62 | 457 | VGYMYWTDWG-EIPKIERAAL-----DGSDRVVLVNT-- | | | SLGWPNGLALDYD |
| | hLRP51 | 162 | HGYMYWTDWG-ETPRIERAGM-----DGSTRKIIVDS-- | | | DIYWPNGLTIDLE |
| | hLRP61 | 149 | SGFMYWTDWG-EVPKIERAGM-----DGSSRFIIINS-- | | | EIYWPNGLTLDYE |
| 4 | hLDLR | 551 | SGRLYWVDSK--LHSISSIDVN-----GGNRKTILEDEK | | | RLAHPFSLAVFE- |
| | mNidogen | 1090 | SSQLCWVDAG--THRAECLNPA-----QPGRRKVLEG-- | | | -LQYPPAVTSYG- |
| | hLRP53 | 815 | DQRLYWTDLD--TNMIESSNML-----GQERVVIADD-- | | | -LPHPFGLTQYS- |
| | hLRP63 | 802 | KRRLYWTDLD--TNLIESSNML-----GLNREVIADD-- | | | -LPHPFGLTQYQ- |
| | hLRP52 | 514 | EGKLYWGDAK--TDKIEVINVD-----GTKRRTILED-- | | | KLPHIFGFTLLG- |
| | hLRP62 | 501 | EGKIYWGDAK--TDKIEVMNTD-----GTGRRVLVED-- | | | KIPHIFGFTLLG- |
| | hLRP51 | 206 | EQKLYWADAK--LSFIHRANLD-----GSFRQKVVEG-- | | | SLTHPFALTLSG- |
| | hLRP61 | 193 | EQKLYWADAK--LNFIHKSNLD-----GTNRQAVVKG-- | | | SLPHPFALTLFE- |
| 5 | hLDLR | 595 | -DKVFWTDII--NEAIFSANRL----TGSDVNLLAEN-- | | | LLSPEDMVLFHN--L |
| | mNidogen | 1131 | -KNLYYTDWK--TNSVIAMDLA----ISKEMDTFHPH-- | | | KQTRLYGITIALSQC |
| | hLRP53 | 856 | -DYIYWTDWN--LHSIERADKT----SGRNRTLIQGH-- | | | LDFVMDILVFHSSRQ |
| | hLRP63 | 843 | -DYIYWTDWS--RRSIERANKT----SGQNRTIIQGH-- | | | LDYVMDILVFHSSRQ |
| | hLRP52 | 556 | -DFIYWTDWQ--RRSIERVHKV----KA-SRDVIIDQ-- | | | LPDLMGLKAVNVAKV |
| | hLRP62 | 543 | -DYVYWTDWQ--RRSIERVHKR----SA-EREVIIDQ-- | | | LPDLMGLKATNVHRV |
| | hLRP51 | 248 | -DTLYWTDWQ--TRSIHACNKR----TGGKRKEIILSA- | | | LYSPMDIQVLSQERQ |
| | hLRP61 | 235 | -DILYWTDWS--THSILACNKY----TGEGLREIHSD-- | | | IFSPMDIHAFSQQRQ |

US 8,716,243 B2

METHODS OF EFFECTING WNT SIGNALING THROUGH DKK STRUCTURAL ANALYSIS

CROSS-REFERENCE TO RELATED U.S. APPLICATIONS

This application claims priority to U.S. Provisional Application No. 61/130,098, filed May 28, 2008 which is incorporated by reference in its entirety herein.

GOVERNMENT FUNDING

This invention was created with Government support under grant number GM081492 awarded by the National Institutes of Health. The Government has certain rights to this invention.

INCORPORATION-BY-REFERENCE & TEXTS

The material in the accompanying sequence listing is hereby incorporated by reference into this application. The accompanying file, named ENZ83.txt, was created on May 20, 2009.

BACKGROUND OF THE INVENTION

1. Technical Field

The present invention is generally directed to compositions and methods related to Wnt signaling regulation by Dickkopf (Dkk) polypeptides.

2. Background Information

Dickkopf (Dkk) proteins are antagonists of the canonical Wnt signaling pathway and are important for embryonic cell fate and bone formation. Abnormal Dkk function has been implicated in cancers, bone diseases, and Alzheimer disease. Wnt antagonism by Dkk involves the binding of the C-terminal cysteine-rich domain of Dkk to Wnt co-receptor, LRP5/6. However, the structural basis of this interaction is unknown.

SUMMARY OF THE INVENTION

This document provides methods and compositions related to Wnt signaling regulation by Dickkopf (Dkk) polypeptides and Wnt-related diseases. The methods and compositions provided herein are based, in part, on the discovery of the molecular interaction between Dkk and LRP5.

Provided in this document are the structure of the Dkk C-terminal cysteine-rich domain and its interactions with LRP5/6. Using NMR spectroscopy, we determined the solution structure of the C-terminal cysteine-rich domain of mouse Dkk2 (Dkk2C2). Then, guided by mutagenesis studies, we docked Dkk2C2 to the YWTD (SEQ ID NO: 19) β-propeller domains of LRP5/6 and showed that the ligand binding site of the third LRP5/6 β-propeller domain matches Dkk2C2 best, suggesting that this domain binds to Dkk2C2 with higher affinity. Such differential binding affinity is likely to play a role in Dkk function in the canonical Wnt pathway.

Provided herein is a compound that disrupts the interaction of a Dickkopf (Dkk) polypeptide with an LDL receptor-related protein (LRP) polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a cysteine-rich domain of a Dkk polypeptide (e.g., Dkk2C or Dkk1C). The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be β-propeller domain of a LRP5 polypeptide (e.g., LRP5-PD1, LRP5-PD2, or LRP5-PD3). The LRP polypeptide can be an LRP6 polypeptide (e.g., a mouse or a human LRP6 polypeptide). The LRP6 polypeptide can be β-propeller domain of a LRP6 polypeptide (e.g., LRP6-PD 1, LRP6-PD2, or LRP6-PD3).

The compound can be a polypeptide. Such a polypeptide can have a sequence having at least 60% identity to SEQ ID NO: 1, SEQ ID NO:2, SEQ ID NO:3, or SEQ ID NO:4.

In some cases, the compound can be a small molecule.

The compound can be a Wnt agonist or antagonist.

In another embodiment, this document provides a compound that disrupts binding of SEQ ID NO:1 to SEQ ID NO:3.

In another embodiment, this document provides a compound that disrupts binding of SEQ ID NO: 1 to SEQ ID NO:4.

In a further embodiment, this document provides a compound that disrupts binding of SEQ ID NO:2 to SEQ ID NO:3.

In another embodiment, this document provides a compound that disrupts binding of SEQ ID NO:2 to SEQ ID NO:4.

This document also provides a compound that forms a hydrogen bond with E721, Y719, and/or D887 of the third propeller domain of human LRP5, and/or a hydrophobic interaction with W780 and/or F888 of the third propeller domain of human LRP5. The hydrogen bond can be with amino acid 77, 79, and/or 245 of SEQ ID NO:3, and the hydrophobic interaction can be with amino acid 138 and/or 246 of SEQ ID NO:3.

Also provided herein is a compound that forms a hydrogen bond with Y706, E708 and/or D874 of the third propeller domain of human LRP6, and/or a hydrophobic interaction with W767 and/or F875 of the third propeller domain of human LRP6. The hydrogen bond can be with amino acid 77, 79, and/or 245 of SEQ ID NO:4, and the hydrophobic interaction can be with amino acid 138 and/or 246 of SEQ ID NO:4.

The compounds can disrupt the interaction of a Dkk polypeptide with an LRP polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD1, LRP6-PD2, or LRP6-PD3.

The compound can be a polypeptide. Such a polypeptide can have a sequence having at least 60% identity to SEQ ID NO: 1 or SEQ ID NO:2.

In some cases, the compound can be a small molecule.

The compound can be a Wnt agonist or antagonist.

Also provided herein is a compound that forms a hydrogen bond with H198, R230, and/or K205 of mouse Dkk2, and/or a hydrophobic interaction with W200, F199, L253, and/or I227 of mouse Dkk2. The hydrogen bond can be with amino acid 27, 59, and/or 34 of SEQ ID NO: 1. The hydrophobic interaction can be with amino acid 28, 29, 82, and/or 56 of SEQ ID NO:1

This document also provides a compound that forms a hydrogen bond with H210, R242, and/or K217 of mouse Dkk1, and/or a hydrophobic interaction with W212, F211, L266, and/or I239 of mouse Dkk1. The hydrogen bond can be with amino acid 27, 59, and/or 34 of SEQ ID NO:2. The hydrophobic interaction can be with amino acid 28, 29, 83, and/or 56 of SEQ ID NO:2.

The compounds can disrupt the interaction of a Dkk polypeptide with an LRP polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD 1, LRP6-PD2, or LRP6-PD3.

The compound can be a polypeptide. Such a polypeptide can have a sequence having at least 60% identity to SEQ ID NO:3, or SEQ ID NO:4.

In some cases, the compound can be a small molecule.

The compound can be a Wnt agonist or antagonist.

Also provided is a composition that modulates Dkk or Wnt activity in a cell, where the composition comprises a compound that disrupts the interaction of a Dkk polypeptide with an LRP polypeptide. The Dkk or Wnt activity can be increased or decreased. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD1, LRP6-PD2, or LRP6-PD3.

The compound can be a polypeptide. Such a polypeptide can have a sequence having at least 60% identity to SEQ ID NO: 1, SEQ ID NO:2, SEQ ID NO:3, or SEQ ID NO:4.

In some cases, the compound can be a small molecule.

The compound can be a Wnt agonist or antagonist.

Provided herein is a method for modulating Dkk or Wnt activity in a cell. The method comprises administering to the cell a compound that disrupts the interaction of a Dkk polypeptide with an LRP polypeptide. The Dkk or Wnt activity can be increased or decreased. The cell can be mammalian (e.g., human, mouse, rat, dog, cat, bovine, or equine). The cell can be an osteoblast or a cancer cell (e.g., colon cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, or bladder cancer). The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD1, LRP6-PD2, or LRP6-PD3. The compound can be a polypeptide. Such a polypeptide can have a sequence having at least 60% identity to SEQ ID NO:1, SEQ ID NO:2, SEQ ID NO:3, or SEQ ID NO:4. In some cases, the compound can be a small molecule.

In another embodiment, this document provides a method for modulating Dkk or Wnt activity in a cell. The method comprises administering to the cell a compound that forms a hydrogen bond with E721, Y719, and/or D887 of the third propeller domain of human LRP5, and/or a hydrophobic interaction with W780 or F888 of the third propeller domain of human LRP5. The hydrogen bond can be with amino acid 77, 79, and/or 245 of SEQ ID NO:3. The hydrophobic interaction can be with amino acid 138 and/or 246 of SEQ ID NO:3.

This document also provides a method for modulating or Wnt activity in a cell. The method comprises administering to the cell a compound that forms a hydrogen bond with Y706, E708 and/or D874 of the third propeller domain of human LRP6, and/or a hydrophobic interaction with W767, or F875 of the third propeller domain of human LRP6. The hydrogen bond can be with amino acid 77, 79, and/or 245 of SEQ ID NO:4. The hydrophobic interaction can be with amino acid 138 and/or 246 of SEQ ID NO:4.

The Dkk or Wnt activity can be increased or decreased. The cell can be mammalian (e.g., human, mouse, rat, dog, cat, bovine, or equine). The cell can be an osteoblast or a cancer cell (e.g., colon cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, or bladder cancer).

The compounds can disrupt the interaction of a Dkk polypeptide with an LRP polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD1, LRP6-PD2, or LRP6-PD3.

The compound can be a polypeptide. Such a polypeptide can have a sequence having at least 60% identity to SEQ ID NO: 1 or SEQ ID NO:2.

In some cases, the compound can be a small molecule.

The compound can be a Wnt agonist or antagonist.

In another embodiment, a method for modulating Dkk or Wnt activity in a cell is provided. The method comprises administering to the cell a compound that forms a hydrogen bond with H198, R230, and/or K205 of mouse Dkk2, and/or a hydrophobic interaction with W200, F199, L253, and/or I227 of mouse Dkk2. The hydrogen bond can be with amino acid 27, 59, and/or 34 of SEQ ID NO: 1. The hydrophobic interaction can be with amino acid 28, 29, 82, and/or 56 of SEQ ID NO: 1

This document also provides a method for modulating Dkk or Wnt activity in a cell, where the method comprises administering to the cell a compound that forms a hydrogen bond with H210, R242, and/or K217 of mouse Dkk1, and/or a hydrophobic interaction with W212, F211, L266, and/or I239 of mouse Dkk1. The hydrogen bond can be with amino acid 27, 59, and/or 34 of SEQ ID NO:2. The hydrophobic interaction can be with amino acid 28, 29, 83, and/or 56 of SEQ ID NO:2.

The Dkk or Wnt activity can be increased or decreased. The cell can be mammalian (e.g., human, mouse, rat, dog, cat, bovine, or equine). The cell can be an osteoblast or a cancer cell (e.g., colon cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, or bladder cancer).

The compounds can disrupt the interaction of a Dkk polypeptide with an LRP polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD1, LRP6-PD2, or LRP6-PD3.

The compound can be a polypeptide. Such a polypeptide can have a sequence having at least 60% identity to SEQ ID NO:3, or SEQ ID NO:4.

In some cases, the compound can be a small molecule.

The compound can be a Wnt agonist or antagonist.

Provided herein is a method for identifying a compound that modulates Dkk or Wnt activity in a cell. The method comprises: a) providing a molecular model of an LRP β-propeller domain; b) designing a query to conduct a conformational search for compounds that fit a receptor site in the LRP β-propeller domain; c) screening a plurality of compounds to identify compounds that meet the requirements of the query; and d) determining whether any one of the identified compounds modulates Dkk or Wnt activity in a cell. The LRP β-propeller domain can be an LRP5-PD (e.g., LRP5-PD1, LRP5-PD2, or LRP5-PD3). The query can be designed using SYBYL® software. The screening can be done using UNITY® software. The determining step can be done using a transcription assay (e.g., by measuring LEF-1 activity or Siamois expression), or by using a Xenopus embryo secondary axis formation model.

The method can further include the step of docking the identified compounds into the receptor site using a computer program, and removing identified compounds that do not dock into the receptor site. Docking can be done using FlexX™ software. In some cases, docking can be done using done using HADDOCK software. Docking done using HADDOCK software can be with an LRP5-PD3, where amino acids Y719, E721, R764, W780, D887, and F888 of said LRP5-PD3 can be defined as active residues, and R652, A653, V694, K697, D718, Q737, G738, N762, G781, P784, R805, W863, H866, and M890 can be defined as passive residues.

The method can further comprise the step of ranking the identified compounds on the basis of their predicted ability to bind to the receptor site. Ranking can be done using Cscore™ software. Ranking can be done using Fscore™ scores.

The method can further comprise the step of determining whether the identified compounds bind to the receptor site using NMR spectroscopy.

The method can further comprise the step of determining the binding affinity of the identified compounds bind to the receptor site using fluorescence spectroscopy.

Provided herein is a method for identifying a compound that modulates Dkk or Wnt activity in a cell. The method comprises: a) providing a molecular model of a Dkk cysteine-rich domain; b) designing a query to conduct a conformational search for compounds that fit a receptor site in the Dkk cysteine-rich domain; c) screening a plurality of compounds to identify compounds that meet the requirements of the query; and d) determining whether any one of the identified compounds modulates Dkk or Wnt activity in a cell. The Dkk cysteine-rich domain can be Dkk2C or a Dkk1C (e.g., Dkk2C2 or Dkk1C2). The query can be designed using SYBYL® software. The screening can be done using UNITY® software. The determining step can be done using a transcription assay (e.g., by measuring LEF-1 activity or Siamois expression), or by using a Xenopus embryo secondary axis formation model.

The method can further include the step of docking the identified compounds into the receptor site using a computer program, and removing identified compounds that do not dock into the receptor site. Docking can be done using FlexX™ software. In some cases, docking can be done using done using HADDOCK software. Docking done using HADDOCK software can be with a Dkk2C2, where amino acids H198, K205, R230, and H254 of said Dkk2C2 are defined as active residues, and E179, F199, W200, T201, L203, P206, E212, V213, K216, Q217, E226, I227, Q229, V241, T246, S249, R252, and L253 are defined as passive residues. Docking done using HADDOCK software can be with a Dkk1C2, where amino acids H210, K217, R242, and H267 of said Dkk1C2 are defined as active residues, and E191, F211, W212, T213, L215, P218, V225, K228, E238, I239, Q241, S261, R265, and L266 are defined as passive residues.

The method can further comprise the step of ranking the identified compounds on the basis of their predicted ability to bind to the receptor site. Ranking can be done using Cscore™ software. Ranking can be done using Fscore™ scores.

The method can further comprise the step of determining whether the identified compounds bind to the receptor site using NMR spectroscopy.

Provided herein is a method of treating a mammal (e.g., a human, mouse, rat, dog, cat, bovine, or equine) having a Wnt-related disease, where the method comprises administering to the mammal a compound that disrupts the interaction of a Dkk polypeptide with an LRP polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a cysteine-rich domain of a Dkk polypeptide (e.g., Dkk2C or Dkk1C). The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be β-propeller domain of a LRP5 polypeptide (e.g., LRP5-PD1, LRP5-PD2, or LRP5-PD3). The LRP polypeptide can be an LRP6 polypeptide (e.g., a mouse or a human LRP6 polypeptide). The LRP6 polypeptide can be β-propeller domain of a LRP6 polypeptide (e.g., LRP6-PD1, LRP6-PD2, or LRP6-PD3).

The compound can be a polypeptide. Such a polypeptide can have a sequence having at least 60% identity to SEQ ID NO: 1, SEQ ID NO:2, SEQ ID NO:3, or SEQ ID NO:4.

In some cases, the compound can be a small molecule.

The compound can be a Wnt agonist or antagonist.

The Wnt-related disease can be cancer (e.g., colon cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, or bladder cancer). The Wnt-related disease can be rheumatoid arthritis, schizophrenia, Alzheimer's disease, or increased bone density.

Also provided herein is a method of treating a mammal (e.g., a human, mouse, rat, dog, cat, bovine, or equine) having a Wnt-related disease, where the method comprises administering to the mammal a compound that forms a hydrogen bond with E721, Y719, and/or D887 of the third propeller domain of human LRP5, and/or a hydrophobic interaction with W780 and/or F888 of the third propeller domain of human LRP5. The hydrogen bond can be with amino acid 77, 79, and/or 245 of SEQ ID NO:3. The hydrophobic interaction can be with amino acid 138 and/or 246 of SEQ ID NO:3.

This document also provides a method of treating a mammal (e.g., a human, mouse, rat, dog, cat, bovine, or equine) having a Wnt-related disease, where the method comprises administering to the mammal a compound that forms a hydrogen bond with Y706, E708 and/or D874 of the third propeller domain of human LRP6, and/or a hydrophobic interaction with W767 and/or F875 of the third propeller domain of human LRP6. The hydrogen bond can be with amino acid 77, 79, and/or 245 of SEQ ID NO:4. The hydrophobic interaction can be with amino acid 138 and/or 246 of SEQ ID NO:4.

The compounds can disrupt the interaction of a Dkk polypeptide with an LRP polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD1, LRP6-PD2, or LRP6-PD3.

The compound can be a polypeptide. Such a polypeptide can have a sequence having at least 60% identity to SEQ ID NO: 1 or SEQ ID NO:2.

In some cases, the compound can be a small molecule.

The compound can be a Wnt agonist or antagonist.

The Wnt-related disease can be cancer (e.g., colon cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, or bladder cancer). The Wnt-related disease can be rheumatoid arthritis, schizophrenia, Alzheimer's disease, or increased bone density.

Provided herein is a method of treating a mammal (e.g., a human, mouse, rat, dog, cat, bovine, or equine) having a Wnt-related disease, where the method comprises administering to the mammal a compound that forms a hydrogen bond with H198, R230, or K205 of mouse Dkk2, and/or a hydrophobic interaction with W200, F199, L253, or I227 of mouse Dkk2. The hydrogen bond can be with amino acid 27, 59, and/or 34 of SEQ ID NO: 1. The hydrophobic interaction can be with amino acid 28, 29, 82, and/or 56 of SEQ ID NO: 1.

This document also provides a method of treating a mammal (e.g., a human, mouse, rat, dog, cat, bovine, or equine) having a Wnt-related disease, where the method comprises administering to the mammal a compound that forms a hydrogen bond with H210, R242, or K217 of mouse Dkk1, and/or a hydrophobic interaction with W212, F211, L266, or I239 of mouse Dkk1. The hydrogen bond can be with amino acid 27, 59, and/or 34 of SEQ ID NO:2. The hydrophobic interaction can be with amino acid 28, 29, 83, and/or 56 of SEQ ID NO:2.

The compounds can disrupt the interaction of a Dkk polypeptide with an LRP polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD1, LRP6-PD2, or LRP6-PD3.

The compound can be a polypeptide. Such a polypeptide can have a sequence having at least 60% identity to SEQ ID NO:3 or SEQ ID NO:4.

In some cases, the compound can be a small molecule.

The compound can be a Wnt agonist or antagonist.

The Wnt-related disease can be cancer (e.g., colon cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, or bladder cancer). The Wnt-related disease can be rheumatoid arthritis, schizophrenia, Alzheimer's disease, or increased bone density.

This document also provides a method of treating a mammal (e.g., a human, mouse, rat, dog, cat, bovine, or equine) having a Wnt-related disease. The method comprises administering to the mammal a composition that modulates Dkk or Wnt activity in a cell, where the composition comprises a compound disrupts the interaction of a Dkk polypeptide with an LRP polypeptide. The Dkk or Wnt activity can be increased or decreased. The cell can be mammalian (e.g., human, mouse, rat, dog, cat, bovine, or equine). The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD 1, LRP6-PD2, or LRP6-PD3. The compound can be a polypeptide. Such a polypeptide can have a sequence having at least 60% identity to SEQ ID NO: 1, SEQ ID NO:2, SEQ ID NO:3, or SEQ ID NO:4. In some cases, the compound can be a small molecule.

The Wnt-related disease can be cancer (e.g., colon cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, or bladder cancer). The Wnt-related disease can be rheumatoid arthritis, schizophrenia, Alzheimer's disease, or increased bone density.

Also provided herein is a composition comprising a compound that disrupts the interaction of a Dkk polypeptide with an LRP polypeptide and a pharmaceutically acceptable carrier. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a cysteine-rich domain of a Dkk polypeptide (e.g., Dkk2C or Dkk1C). The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be β-propeller domain of a LRP5 polypeptide (e.g., LRP5-PD1, LRP5-PD2, or LRP5-PD3). The LRP polypeptide can be an LRP6 polypeptide (e.g., a mouse or a human LRP6 polypeptide). The LRP6 polypeptide can be β-propeller domain of a LRP6 polypeptide (e.g., LRP6-PD1, LRP6-PD2, or LRP6-PD3).

The compound can be a polypeptide. Such a polypeptide can have a sequence having at least 60% identity to SEQ ID NO: 1, SEQ ID NO:2, SEQ ID NO:3, or SEQ ID NO:4.

In some cases, the compound can be a small molecule.

The compound can be a Wnt agonist or antagonist.

The composition can be formulated for administration by inhalation, oral, intravenous, intraperitoneal, intramuscular, parenteral, transdermal, intravaginal, intranasal, mucosal, sublingual, topical, rectal, or subcutaneous administration. The composition can be formulated as a pill, a tablet, a dragee, a liquid, a gel, a capsule, a syrup, a slurry, or a suspension.

Provided herein is a composition comprising a compound and a pharmaceutically acceptable carrier, where the compound forms a hydrogen bond with E721, Y719, and/or D887 of the third propeller domain of human LRP5, and/or a hydrophobic interaction with W780 and/or F888 of the third propeller domain of human LRP5. The hydrogen bond can be with amino acid 77, 79, and/or 245 of SEQ ID NO:3. The hydrophobic interaction can be with amino acid 138 and/or 246 of SEQ ID NO:3.

This document also provides a composition comprising a compound and a pharmaceutically acceptable carrier, where the compound forms a hydrogen bond with Y706, E708 and/or D874 of the third propeller domain of human LRP6, and/or a hydrophobic interaction with W767 and/or F875 of the third propeller domain of human LRP6. The hydrogen bond can be with amino acid 77, 79, and/or 245 of SEQ ID NO:4. The hydrophobic interaction can be with amino acid 138 and/or 246 of SEQ ID NO:4.

The compounds can disrupt the interaction of a Dkk polypeptide with an LRP polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD1, LRP6-PD2, or LRP6-PD3.

The compound can be a polypeptide. Such a polypeptide can have a sequence having at least 60% identity to SEQ ID NO: 1 or SEQ ID NO:2.

In some cases, the compound can be a small molecule.

The compound can be a Wnt agonist or antagonist.

The composition can be formulated for administration by inhalation, oral, intravenous, intraperitoneal, intramuscular, parenteral, transdermal, intravaginal, intranasal, mucosal, sublingual, topical, rectal, or subcutaneous administration. The composition can be formulated as a pill, a tablet, a dragee, a liquid, a gel, a capsule, a syrup, a slurry, or a suspension.

Further provided herein is a composition comprising a compound and a pharmaceutically acceptable carrier, where the compound forms a hydrogen bond with H198, R230, and/or K205 of mouse Dkk2, and/or a hydrophobic interaction with W200, F199, L253, and/or I227 of mouse Dkk2. The hydrogen bond can be with amino acid 27, 59, and/or 34 of SEQ ID NO: 1. The hydrophobic interaction can be with amino acid 28, 29, 82, and/or 56 of SEQ ID NO: 1.

This document also provides a composition comprising a compound and a pharmaceutically acceptable carrier, where the compound forms a hydrogen bond with H210, R242, or K217 of mouse Dkk1, and/or a hydrophobic interaction with W212, F211, L266, and/or I239 of mouse Dkk1. The hydrogen bond can be with amino acid 27, 59, and/or 34 of SEQ ID NO:2. The hydrophobic interaction can be with amino acid 28, 29, 83, and/or 56 of SEQ ID NO:2.

The compounds can disrupt the interaction of a Dkk polypeptide with an LRP polypeptide. The Dkk polypeptide can be a Dkk2 polypeptide or a Dkk1 polypeptide. The Dkk polypeptide can be a mouse Dkk polypeptide or a human Dkk polypeptide. The Dkk polypeptide can be a Dkk2C or Dkk1C. The cysteine-rich domain of a Dkk polypeptide can be a Dkk2C2 or a Dkk1C2. The LRP polypeptide can be an LRP5 polypeptide (e.g., a mouse or a human LRP5 polypeptide). The LRP5 polypeptide can be an LRP5-PD1, LRP5-PD2, or LRP5-PD3. The LRP polypeptide can be an LRP6 polypeptide (e.g., a mouse or a human LRP6 polypeptide). The LRP6 polypeptide can be an LRP6-PD 1, LRP6-PD2, or LRP6-PD3.

The compound can be a polypeptide. Such a polypeptide can have a sequence having at least 60% identity to SEQ ID NO:3 or SEQ ID NO:4.

In some cases, the compound can be a small molecule.

The compound can be a Wnt agonist or antagonist.

The composition can be formulated for administration by inhalation, oral, intravenous, intraperitoneal, intramuscular, parenteral, transdermal, intravaginal, intranasal, mucosal, sublingual, topical, rectal, or subcutaneous administration. The composition can be formulated as a pill, a tablet, a dragee, a liquid, a gel, a capsule, a syrup, a slurry, or a suspension.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the detailed description set forth below. Other features, objects, and advantages of the invention will be apparent from the description and drawings, and from the claims.

DESCRIPTION OF THE DRAWINGS

FIG. 2 discloses SEQ ID NOS 1, 5-6, 2 and 7-12, respectively, in order of appearance.

FIG. 6. Sequence alignment of YWTD (SEQ ID NO: 19) β-propeller domains. Structural alignment of mouse nidogen-1 and human LDL receptor β-propeller domains and alignment by sequence to the YWTD (SEQ ID NO: 19) β-propeller domains of human LRP5/6. m indicates mouse; h indicates human; the suffixes 1, 2, and 3 refer to the first, second, and third β-propeller domains of LRP5/6, respectively. Each row corresponds to one YWTD (SEQ ID NO: 19) repeat; the offset blade boundaries are indicated by grey lines. Blades are structurally aligned, and β strands of nidogen-1 and LDLR β-propeller domains are underlined. Residues in the third propeller of human LRP5 (hLRP53) known to comprise the Dkk 1/2 binding interface are denoted by boldface type. Residues in nidogen-1 which contact with LE4 or LE3 modules of laminin are in boldface type. FIG. 6 discloses SEQ ID NOS 13-14, 3-4 and 15-18, respectively, in order of appearance.

DETAILED DESCRIPTION

Figure 1:
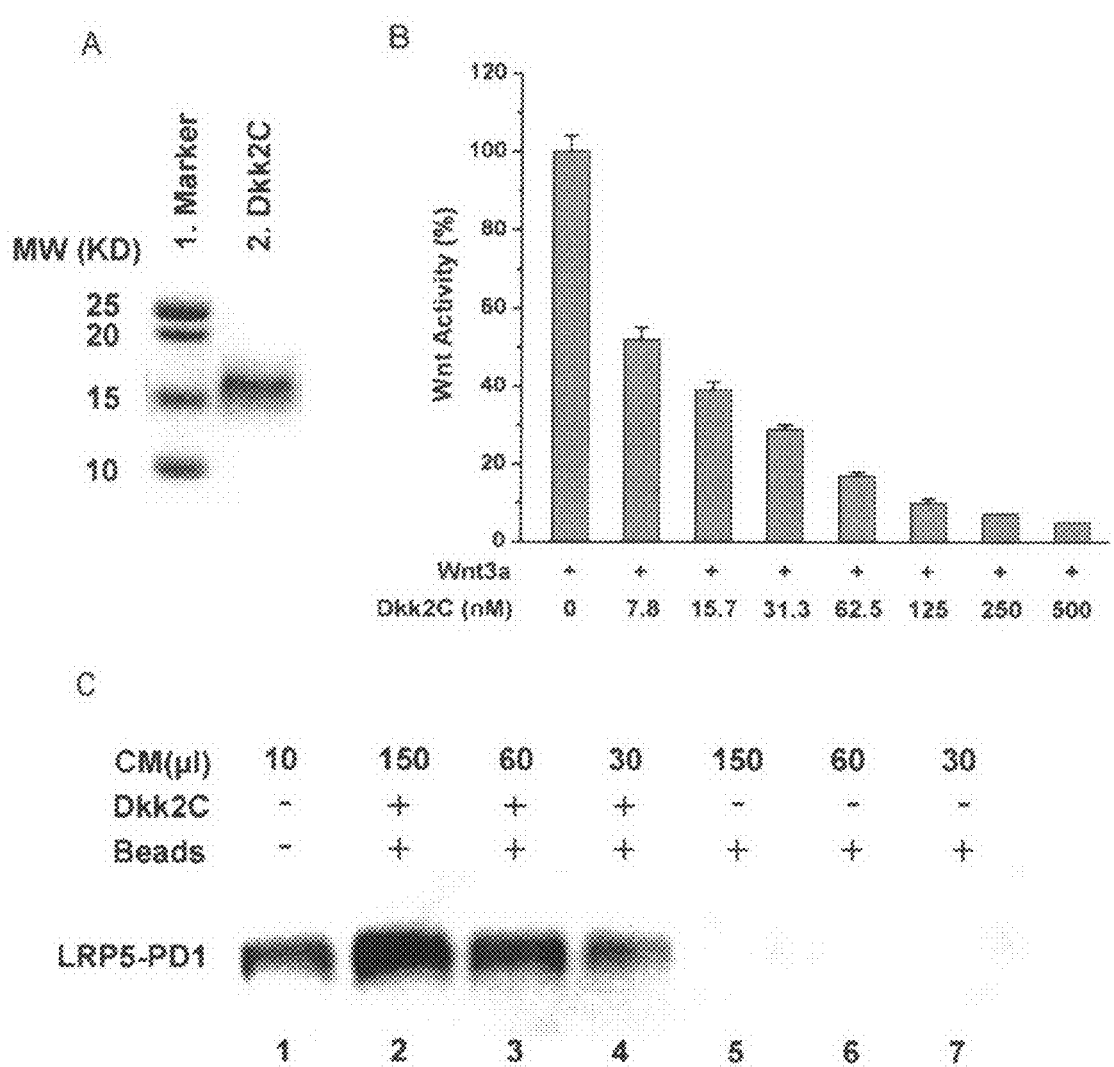
FIG. 1. Inhibition of Wnt3a activities mediated by recombinant Dkk2C2. A, SDS-PAGE of recombinant Dkk2C2 expressed and purified from an *E. coli* system. B, effects of Dkk2C2 on canonical Wnt signaling activity. NIH3T3 cells were transfected with a LEF-1 luciferase reporter plasmid and a green fluorescent protein expression plasmid. The next day, cells were treated with Dkk2C2 solution with the indicated concentrations and Wnt3a conditioned medium (50 ng/ml) for 6 h. The cells were then lysed, and luciferase activities were determined and normalized against the green fluorescent protein levels after 6 h. The activity from cells treated with Wnt3a only was taken as 100%. Two experiments were done individually, and the average values were taken as the results. C, in vitro binding of Dkk2C2 to LRP5-PD1 detected by pulldown experiments and Western blotting assay. LRP5-PD1-HA-containing conditioned medium (CM) in the indicated volume was incubated with purified S-tagged Dkk2C2-coupled S-protein-agarose (lanes 2-4) or with S-protein-agarose only (lanes 5-7), respectively. After extensive washing, LRP5-PD1 bound to Dkk2C2 were detected using an HA antibody specific to an HA tag carried by LRP5-PD1 in Western blotting assay. Lane 1, expression of LRP5-PD1 in conditioned medium was detected by HA antibody.

The present invention is directed to compositions and methods related to Dkk regulation of Wnt signaling. A composition related to Dkk regulation of Wnt signaling typically binds to a Dkk cysteine-rich domain or an LRP β-propeller domain. In some cases, such a composition interferes with binding of a Dkk polypeptide to an LRP polypeptide. Such compositions and methods can be used to modulate Dkk or Wnt activity in a cell or treat a Wnt-related disease, such as one caused by abnormal Dkk function (e.g., cancer, bone disease, and Alzheimer disease).

Dkk proteins are antagonists of the canonical Wnt signaling pathway, and are important for embryonic cell fate and bone formation. Abnormal Dkk function has been implicated in cancers, bone diseases, and Alzheimer's disease [1]. Dkk proteins (e.g., Dkk1 and Dkk2) are composed of two characteristic cysteine-rich domains, termed as N-terminal (e.g., Dkk1C1 and Dkk2C1), and C-terminal (e.g., Dkk1C2 and Dkk2C2) cysteine-rich domains, each containing ten conserved cysteines separated by a variable-length spacer region [2]. Wnt antagonism by Dkk involves the binding of the C-terminal cysteine-rich domain of Dkk to the Wnt co-receptor, LDL receptor-related protein 5 or 6 (i.e., LRP5 or LRP6, respectively). The Dkk-LRP5/6 complex antagonizes canonical Wnt signaling by inhibiting LRP5/6 interaction with Wnt and by forming a ternary complex with the transmembrane protein Kremen, which promotes internalization of LRP5/6

The Dkk family has at least four members (e.g., Dkk1, Dkk2, Dkk3, and Dkk4). Dkk1 and Dkk2 share 50% identity in their N-terminal cysteine-rich domains and 70% identity in their C-terminal cysteine-rich domains. We previously found that the C-terminal domain of human DKK1 and 2, which contains the second cysteine-rich region, is sufficient for antagonism of Wnt activity in mammalian cells. The same was also found to be true in *Xenopus*; the C-terminal domain of Dkk1 and 2 is both necessary and sufficient to inhibit Wnt-stimulated induction of secondary axis development and transcriptional activation of the *Siamois* promoter, cooperate with a dominant-negative BMP4 receptor to induce head structure development, and physically associate with LRP5/6.

As used herein, the terms Dkk1C and Dkk2C refer to either of the cysteine-rich domains of Dkk1 and Dkk2, respectively. The terms Dkk1C1 and Dkk2C1 refer to the N-terminal cysteine-rich domains of Dkk1 and Dkk2, respectively. The terms Dkk1C2 and Dkk2C2 refer to the C-terminal cysteine-rich domains of Dkk1 and Dkk2, respectively.

Compounds and Compositions

The compounds provided herein typically bind a Dkk polypeptide or an LRP polypeptide. In some cases, a compound provided herein compound can bind to a full-length Dkk protein or a portion thereof (e.g., a Dkk cysteine-rich domain). Such a portion can be an N-terminal Dkk cysteine-rich domain (e.g., Dkk1C1 or Dkk2C1) or a C-terminal Dkk cysteine-rich domain (e.g., Dkk1C2 or Dkk2C2). In other cases, a compound provided herein can bind a full-length LRP protein or a portion thereof (e.g., an LRP5/6 β-propeller domain). An LRP β-propeller domain (LRP-PD) can be any one of six β-propeller domains in each of LRP5 or LRP6. For example, an LRP-PD can be a first, second, or third propeller domain of LRP5 (i.e., LRP5-PD1, LRP5-PD2, or LRP5-PD3, respectively) or a first, second, or third propeller domain of LRP6 (i.e., LRP6-PD1, LRP6-PD2, or LRP6-PD3, respectively). Typically, the compounds provided herein bind a mammalian (e.g., human, mouse, rat, dog, cat, bovine, or equine) Dkk or LRP polypeptide, but can also bind Dkk or LRP polypeptides from other sources, such as *Xenopus*.

A compound provided herein can interact with specific amino acid residues of a Dkk polypeptide or an LRP polypeptide. Such interactions can be hydrogen bonds and/or hydrophobic interactions. For example, such a compound can form hydrogen bonds or hydrophobic interactions with particular amino acid residues of a Dkk polypeptide. For example, a compound can form a hydrogen bond with one or more amino acid residues (e.g., H198, R230, and/or K205) of mouse Dkk2, or the corresponding amino acid residues in SEQ ID NO: 1. In another example, a compound can form a hydrogen bond with one or more amino acid residues (e.g., H210, R242, and/or K217) of mouse Dkk1, or the corresponding amino acid residues in SEQ ID NO:2. In other cases, a compound can form a hydrophobic interaction with one or more amino acid residues (e.g., W200, F199, L253, and/or I227) of mouse Dkk2, or the corresponding amino acid residues in SEQ ID NO: 1. In yet other cases, a compound can form a hydrophobic interaction with one or more amino acid residues (e.g., W212, F211, L266, and/or I239) of a mouse Dkk1, or the corresponding amino acid residues in SEQ ID NO:2.

In another example, a compound provided herein can form hydrogen bonds or hydrophobic interactions with an LRP polypeptide. For instance, a compound can form a hydrogen bond with one or more amino acid residues (e.g., E721, Y719, and/or D887) of human LRP5, or the corresponding amino acid residues in SEQ ID NO:3. In other cases, a compound can form a hydrogen bond with one or more amino acid residues (e.g., Y706, E708, and/or D874) of human LRP6, or the corresponding amino acid residues in SEQ ID NO:4. In yet other cases, a compound can form a hydrophobic interaction with one or more amino acid residues (e.g., W780 and/or F888) of human LRP5, or the corresponding amino acid residues in SEQ ID NO:3. In other instances, a compound can form a hydrophobic interaction with one or more amino acid residues (e.g., W767 and/or F875), or the corresponding amino acid residues in SEQ ID NO:4.

It is understood that a single compound can form both hydrogen bonds and hydrophobic interactions with a single Dkk polypeptide or LRP polypeptide.

A compound provided herein can bind with an affinity that is less than, equal to, or greater than a natural ligand that binds a Dkk polypeptide or an LRP polypeptide. For example, a compound provided herein can bind with a lower affinity to a Dkk2C2 than an LRP5-PD3. In another example, a compound provided herein can bind with equal or greater affinity to an LRP5-PD3 than a Dkk1C2. In some cases, such compounds and compositions disrupt the interaction of a Dkk (e.g., a Dkk2 or a Dkk1) polypeptide with an LRP (e.g., and LRP5 or an LRP6) polypeptide. For example, a compound can disrupt binding between a polypeptide comprising SEQ ID NO: 1 and a polypeptide comprising SEQ ID NO:3. In another example, a compound can disrupt binding between a polypeptide comprising SEQ ID NO: 1 and a polypeptide comprising SEQ ID NO:4. In yet another example, a compound provided herein can disrupt binding between a polypeptide comprising SEQ ID NO:2 and a polypeptide comprising SEQ ID NO:3 or SEQ ID NO:4.

The compounds provided herein can modulate (e.g., increase or decrease) Dkk or Wnt activity in a cell. Such cells can be mammalian (e.g., human, mouse, rat, dog, cat, bovine, or equine, or from any other source, such as *Xenopus*. A compound is said to modulate Dkk or Wnt activity when an indicator or Dkk or Wnt activity (e.g., TCF/LEF-1 transcriptional activity, Wnt-responsive gene expression, or *Xenopus* embryo secondary axis formation) is increased or decreased when said compound is administered to the appropriate cell type.

The compounds provided herein can be any appropriate compound. For example, a compound provided herein can be a polypeptide. As used herein, the term "polypeptide" refers to a compound of two or more subunit amino acids, amino acid analogs, or other peptidomimetics. The subunits may be linked by peptide bonds or other bonds, such as, for example, ester or ether bonds. The term "amino acid" refers to natural and/or unnatural or synthetic amino acids, including D/L optical isomers.

In some cases, a compound provided herein can comprise an amino acid sequence comprising a sequence having 60% or greater sequence (e.g., 65%, 70%, 75%, 80%, 85%, 90%, 95%, or 100%) identity to any of the sequences set forth in SEQ ID NO: 1, SEQ ID NO:2, SEQ ID NO:3, or SEQ ID NO:4. In polypeptides that have less than 100% identity to the sequences set forth in SEQ ID NO: 1, SEQ ID NO:2, SEQ ID NO:3, or SEQ ID NO:4, amino acid residues identified as being involved in binding to a Dkk polypeptide or an LRP polypeptide can be conserved or can be substituted with conservative mutations. For example, amino acids 27-29, 34, 56, 59, 82, and 83 of SEQ ID NO: 1 can be conserved or substituted with conservative mutations. In another example, amino acids 27-29, 34, 56, 59, 83, and 84 of SEQ ID NO:2 can be conserved or substituted with conservative mutations. In another example, amino acids 77, 79, 138, 245, and 246 of SEQ ID NO:3 can be conserved or substituted with conservative mutations. In yet another example, amino acids 77, 79, 138, 245, and 246 of SEQ ID NO:4 can be conserved or substituted with conservative mutations.

In some cases, a compound provided herein can be a small molecule. The small molecule compounds provided herein can be organic or inorganic. Small molecule compounds can be obtained from small molecule libraries such as those maintained at the Developmental Therapeutics Program (DTP) at the National Cancer Institute (NCI).

Compounds provided herein can be identified as binding to a Dkk polypeptide or an LRP polypeptide using any suitable means. For example, a compound provided herein can be identified as binding to a Dkk polypeptide or an LRP polypeptide using in silico, in vitro, or in vivo methods, or any combination thereof.

In some cases, a compound is identified as binding to a Dkk polypeptide or an LRP polypeptide by determining whether the compound modulates Dkk or Wnt activity in a cell. Such a method can include providing a molecular model of an LRP polypeptide or a Dkk polypeptide using an appropriate computer program, designing a query to conduct a conformational search for compounds that fit a receptor site in the respective LRP polypeptide or Dkk polypeptide, screening a plurality of compounds to identify compounds that meet the criteria of the query, and determining whether any of the identified compounds modulates Dkk or Wnt activity in a cell. Such a method can be done using any appropriate tools. For example, a query can be designed using SYBYL® software. In another example, screening can be done using UNITY® software. The determining step can be done using a transcription assay (e.g., LEF-1 activity or *Siamois* expression) or by using a *Xenopus* embryo secondary axis formation assay.

In some cases, methods for identifying a compound that binds a Dkk or LRP polypeptide can include a step of docking compounds into the appropriate Dkk or LRP molecular model. Docking can be done using, for example, FlexX™ software or HADDOCK software. In cases where HAD- DOCK software is used, amino acids in either the Dkk polypeptide or the LRP polypeptide that have been identified as being involved in the ability to modulate Wnt signaling in a cell can be designated as active residues, while other surface amino acids can be identified as passive.

Additional steps for identifying the provided compounds can include ranking identified compounds on the basis of their predicted ability to bind the receptor site using, for example, Cscore™ software; determining whether identified compounds bind to the receptor site using NMR spectroscopy; and/or determining the binding affinity of the identified compounds using, for example, fluorescence spectroscopy.

The compounds provided herein can be included in various compositions. Any appropriate composition is provided herein. For example, a compound provided herein can be included in a therapeutic composition. A composition provided herein can comprise a provided compound and a pharmaceutically acceptable carrier. Such compositions can be formulated to be administered by any appropriate route (e.g., inhalation, oral, intravenous, intraperitoneal, intramuscular, parenteral, transdermal, intravaginal, intranasal, mucosal, sublingual, topical, rectal or subcutaneous). Compositions provided herein can be formulated as a pill, a tablet, a dragee, a liquid, a gel, a capsule, a syrup, a slurry, a suspension, or any other appropriate formulation.

Methods

The provided compounds and compositions can be used in the methods provided herein. For example, the compounds provided herein can be used to modulate (e.g., increase or decrease) Dkk or Wnt activity in a cell.

In some cases, compounds and compositions provided herein can be used to treat a mammal having a Wnt-related disease. For example, the compounds and compositions provided herein can be administered to a mammal in an amount and at a frequency sufficient to reduce or prevent the symptoms of the disease to be treated. Such diseases can include, for example, cancer (e.g., colon, breast, melanoma, head and neck, lung, non-small-cell lung, gastric, mesothelioma, Barrett's esophagus, synovial sarcoma, cervical, leukemia, prostate, and bladder), rheumatoid arthritis, schizophrenia, Alzheimer's disease, and bone disease (e.g., increased bone density).

Articles of Manufacture

Also provided herein are articles of manufacture that comprise a compound or composition provided herein. The articles of manufacture can include appropriate packaging material, such as, but not limited to labels. Articles of manufacture provided herein can also include means of delivering the provided compounds or compositions to a cell or mammal. Such means include reagents for transfection or syringes.

The invention will be further described in the following examples, which do not limit the scope of the invention described in the claims.

EXAMPLES

Example 1

Dkk2C2-Mediated Inhibition of Wnt Activity

The recombinant protein Dkk2C2 (amino acids Met[172]-Ile[259] of mouse Dkk2) was expressed and purified from an *Escherichia coli* system as described previously [1,1]. The recombinant protein contained an N-terminal S tag and a thrombin cleavage site between the S tag and Dkk2C2. The purified recombinant Dkk2C2 contained only one single band in SDS-PAGE (FIG. 1A). NIH3T3 cells were seeded in 24-well plates at $4\times10^5$ cells/well and transfected with a LEF-1 luciferase reporter plasmid, an enhanced green fluorescent protein plasmid, and LacZ plasmid (total 0.5 µg of DNA/well) by using Lipofectamine and Plus reagent (Invitrogen), as suggested by the manufacturer. 24 h after transfection, cells were treated with Wnt3a conditioned medium and different dosages of purified Dkk2C2 for 6 h. Cells were treated with Wnt3a and vehicle as the control for 6 h. Then cells were lysed, and luciferase activity in the cell lysate was measured as described previously [12]. Luminescence intensity, which represents Wnt activity, was normalized against the fluorescence intensity of enhanced green fluorescent protein.

The Dkk2C2 possessed a significant inhibitory activity on canonical Wnt signaling; it inhibited Wnt3a activities with an $IC_{50}$ value around 8 nM in the Wnt reporter gene assay (FIG. 1B), indicating the protein we produced is functional.

Example 2

S-Protein Pulldown Experiments and Western Blotting Analysis

For preparation of the first β-propeller domain of mouse LRP5 with HA tag (LRP5-PD 1-HA)-containing conditioned medium, HEK cells were seeded in 6-well plates at $4\times10^5$ cells/well and transfected with 1 µg of DNA/well. The conditioned medium was collected 30 h after transfection by centrifugation.

S-protein-agarose was obtained from Novagen, and the pulldown experiments were conducted in accordance with a standard protocol provided by the manufacturer. Briefly, for each pulldown experiment, 300 µl of S-tagged Dkk2C2 (5 µM) was incubated with 200 µl of S-protein-agarose at room temperature for 2 h with gentle agitation to allow the binding of S-tagged Dkk2C2 to S-protein-agarose, followed by washing four times to remove the unbound Dkk2C2 by centrifugation. Then, the S-tagged Dkk2C2-charged agarose was incubated with the LRP5-PD1-HA conditioned medium in indicated concentrations at 4° C. for 4 h with gentle agitation. After the agarose was washed three times with buffer, it underwent SDS-PAGE and then Western blotting analysis. Western blotting analysis was performed following a standard protocol by using mouse monoclonal IgG3 against an HA tag (from Millipore) as the primary antibody and goat anti-mouse horseradish peroxidase-conjugated IgG (from Cell Signaling Technology) as the secondary antibody. Finally, the membrane was incubated in SuperSignal West Femto maximum sensitivity substrate (Pierce) at room temperature for 5 min., and the results were developed on the film (Eastman Kodak Co.).

In vitro pulldown experiments showed that Dkk2C2 directly bound to the first propeller domain of LRP5 (LRP5-PD1), further confirming that the protein we produced is well folded and functional (FIG. 1C).

Example 3

Structural Determination of the Solution Structure of Dkk2C2

The method used to determine the solution structure of Dkk2C2 is similar to those described previously [11, 13]. Briefly, the $^{13}C/^{15}N$ double-labeled protein was produced in an *E. coli* system, and the N-terminal S tag was removed by thrombin. Typical NMR samples consisted of 1 mM $^{15}N/^{13}C$-

Dkk2C2 in 5 mM D4-acetic acid (pH 5.0) buffer with 10% (v/v) D$_2$O. All NMR experiments were performed with Bruker 600- and 800-MHz NMR spectrometers at 25° C. NMR spectra were processed and displayed by the NMRPipe [14] software package. The program XEASY [15] was used for data analysis and structure assignment. Backbone assignment was based mainly on HNCA, HN(CO)CA, HNCACB, and CBCA(CO)NH experiments. Side chain proton resonance was assigned by using $^{15}$N HSQC-TOCSY and HCCH-TOCSY. Aromatic side chain proton resonance was assigned with CB(CGCD)HD and CB(CGC-DCE)HE experiments. NOE distance constraints were obtained from NOE peaks in two-dimensional $^1$H-$^1$H NOE spectroscopy, three-dimensional $^{15}$N HSQC-NOE spectroscopy, and three-dimensional $^{13}$C HSQC-NOE spectroscopy experiments.

Intensities of NOE peaks were calibrated and converted to distance constraints by the program CALIBA [16] CYANA2.1 [17] software was used for structure calculations, which were based on 1,879 proton-proton distance constraints and 112 dihedral angle restraints. Through the space proximity, the five disulfide bridges within the structure could be clearly identified in the earlier structural calculations. Based on such information, 30 disulfide distance constraints (three upper limits and three lower limits for each disulfide bridge) were added in the final structural calculation. The superimposition of backbone atoms of 20 conformers with smallest target function values among 200 calculated structures yielded a root mean square deviation of 0.36±0.11 Å relative to the average structure, and the average target function value of ensemble structures was 1.57±0.15 Å$^2$ with no distance violations >0.2 Å or dihedral angle violations >5°. The statistical characteristics of these 20 best conformers are described in Table 1.

Figure 2:
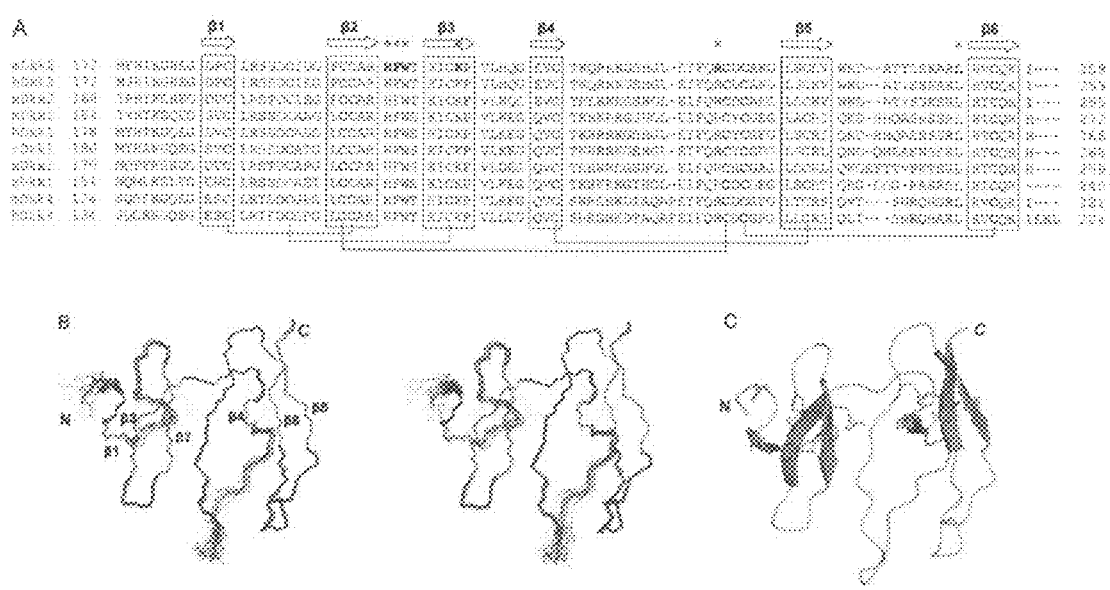
FIG. 2. Solution structure of Dkk2C2. A, amino acid sequence alignment of C-terminal cysteine-rich domains of Dkks in mouse (m), human (h), *Xenopus* (x), rabbit (r), and zebrafish (z). β strand elements identified in the three-dimensional structure of Dkk2C2 are indicated at the top. Ten conserved cysteines are in bold type, and pairs of cysteines forming disulfide bridges are colored identically and linked by lines. Amino acids that contact the third β-propeller domain of LRP5 in the docked model are in bold and indicated by the dots. B, stereo view of the peptide backbone (N, C-α, C') determined by superimposition of 20 conformers of Dkk2C2 with the lowest target function values. The figure was generated by using MOLMOL [39]. C, ribbon diagram of Dkk2C2 with the lowest target function values, generated by using MOLSCRIPT [40].
Figure 3:
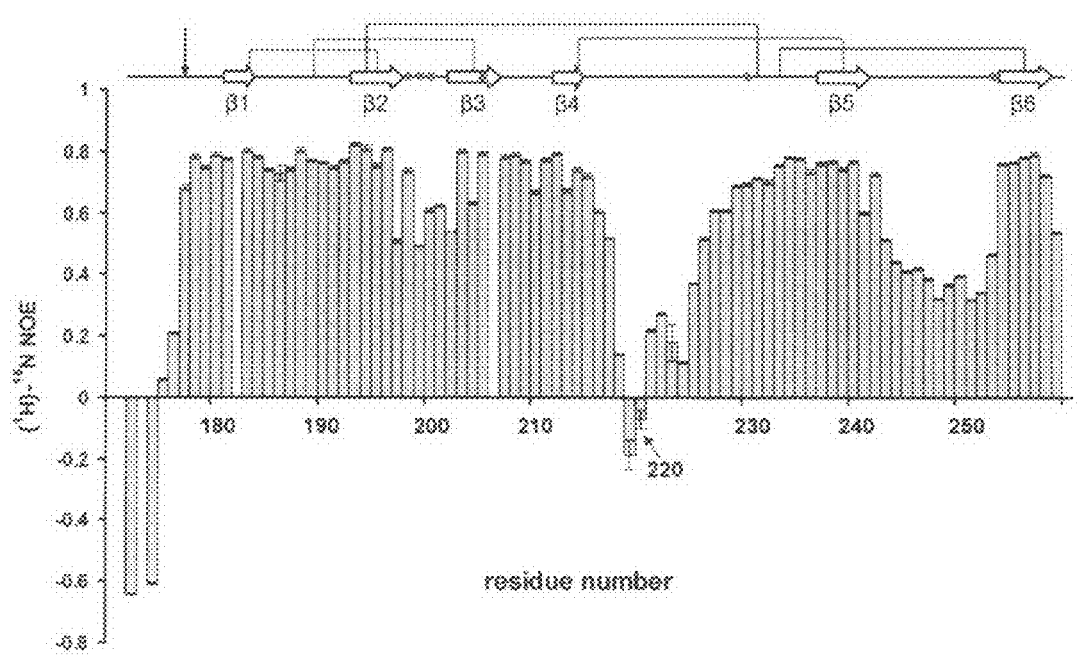
FIG. 3. Plot of backbone amide heteronuclear $^{15}N[^1H]$ NOE values versus residue number for the Dkk2C2. The steady-state heteronuclear $^{15}N[^1H]$NOE value is plotted versus the residue number measured with a Bruker 600-MHz spectrometer at 25° C. The secondary structure elements and disulfide brides in the Dkk2C2 are indicated at the top; amino acids that contact the third β-propeller domain of LRP5 in the docked model are indicated by the dots. Because the lengths of the N—H bonds are fixed, the $^{15}N[^1H]$NOE provides information about the dynamics of N—H bonds that can be used to determine whether a particular amide is in a well folded or a flexible region of a protein. The arrow indicates the starting residue, $Gly^{177}$, of the folded Dkk2C2.

The solution structure of Dkk2C2 can be found in FIG. 2A. The structure was well defined except for one loop region and the N-terminal region (FIG. 2B and Table 1), and the five disulfide bonds were clearly identified. Within the structure of Dkk2C2 are two subdomains sharing very similar topology; each has a central anti-parallel β-sheet region consisting of three β strands (β1-β3 in subdomain 1 and β4-β6 in subdomain 2) and two finger-shaped loops linking the three β strands (FIG. 2C). The second subdomain has longer and flexible "finger loops" and is thus much larger than the first one. The flexibilities of the two finger loops in the second subdomain are clear in the relaxation data. The steady-state heteronuclear $^{15}$N[$^1$H]NOE values versus the residue number of Dkk2C2 are shown in FIG. 3. Because the lengths of the N—H bonds are fixed, the $^{15}$N[$^1$H]NOE values report information about the dynamics of N—H bonds and are used to determine the motion of a particular residue [21]. Typically, the value for the heteronuclear $^{15}$N[$^1$H]NOE of folded residues is ~1-0.7, and the NOE for a flexible loop is <0.5. The dynamic study showed that the first finger loop in the second subdomain (loop β4-β5) is most flexible. The study also showed that the folded Dkk2C2 should start at Gly$^{177}$.

Within each subdomain are two disulfide bonds to stabilize the β-core region; one connects the first and second β-sheets (Cys$^{183}$-Cys$^{195}$ connecting β1 and β2 in the subdomain 1 and Cys$^{214}$-Cys$^{239}$ connecting β4 and β5 in subdomain 2), and another (Cys$^{189}$-Cys$^{204}$ and Cys$^{233}$-Cys$^{256}$) connects the third β sheet (β3 and β6, respectively) to the first finger loop (loop β1-β2 and loop β4-β5, respectively). The fifth disulfide bond (Cys$^{194}$-Cys$^{231}$) links the two subdomains together. The five dihedral angles in each of five disulfide bonds in the solution structure of Dkk2C2 are well within the range of the established stereochemical preferences of a single disulfide bridge [22]. Among the five disulfide bonds in the Dkk2C2 structure, only the first one (Cys$^{183}$-Cys$^{195}$) has the right-handed conformation; the rest of the four disulfide bonds are all in the left-handed conformation [23].

The atomic coordinates and structure factors for Dkk2C2 have been deposited in the Protein Data Bank (PDB), Research Collaboratory for Structural Bioinformatics, Rutgers University, New Brunswick, N.J. (http://www.rcsb.org/) as PDB identification number 2JTK.

Analysis with DALI [24] software showed that the Dkk2C2 structure shares some features with those of colipase (Protein Data Bank code 1 PCN) [25] and MIT1 (mamba intestinal toxin 1) (Protein Data Bank code 1IMT) [26], which belong to a family of proteins lacking extensive secondary structures and stabilized by abundant disulfide bridges [27]. All three can be described as an assembly of protruding fingers, held together at one end by a network of five disulfide bridges. However, only the two central β-core regions of Dkk2C2, colipase, and MIT1 are similar, and the connectivity patterns of disulfide bridges among the three proteins share a highly conserved feature [23]. Indeed, the sequence identity shared by Dkk2C2 with the two proteins (24% with colipase and 29% with MIT1) is concentrated in the two central β-core regions, all of the finger-loop regions of Dkk2C2 are unique, and each has a different length and conformation.

TABLE 1

Statistical characteristics of the 20 conformers of the solution structure of Dkk2C2

| Parameter | |
|---|---|
| No. of NOE distance restraints | |
| Intraresidue | 448 |
| Interresidue | |
| Sequential | 561 |
| Medium range | 243 |
| Long range | 627 |
| Total | 1879 |
| No. of disulfides restraints | 30 |
| No. of Talos dihedral angle restraints | |
| Φ | 56 |
| Ψ | 56 |
| R.M.S. deviations from the mean (Å)$^a$ | |
| Overall structure,$^b$ backbone | 0.36 ± 0.11 |
| Gly$^{177}$-Gln$^{217}$ and Glu$^{226}$-Ile$^{259}$, backbone | 0.18 ± 0.04 |
| Overall structure,$^b$ heavy atoms | 0.82 ± 0.10 |
| Gly$^{177}$-Gln$^{217}$ and Glu$^{226}$-Ile$^{259}$, heavy atoms | 0.68 ± 0.10 |
| Residues$^b$ in Ramachandran plot (%)$^c$ | |
| Most favorable regions | 84.7 |
| Additionally allowed regions | 13.4 |
| Generously allowed regions | 1.9 |
| Disallowed regions | 0.0 |

$^a$The average root mean square deviation (r.m.s.d.) between the 20 structures with the lowest target functions and the mean coordinates of the protein.
$^b$Residues Gly$^{177}$-Ile$^{259}$.
$^c$Excluding glycines and prolines and calculated using the Ramachandran macro in CYANA software.

Example 4

Mutagenesis Studies

To determine the effect of representative point mutants of Dkk 1 on the inhibition of Wnt activity [10], NIH3T3 cells were transfected with LEF-1 luciferase reporter plasmids and 1 day later were treated with Wnt3a conditioned medium and Dkk1 or Dkk1 mutants conditioned medium prepared from HEK cells for 6 h. Then luciferase activity was measured as described above. To measure the binding of Dkk1 and its mutants to LRP6, HEK cells were transfected with LRP6 plasmids and 1 day later were incubated on ice with wild-type or mutant Dkk1-alkaline phosphatase (AP) fusion protein conditioned medium for 2 h [10]. Then the cells were washed and lysed, and AP activity in cell lysate was measured by using a Tropix luminescence AP assay kit as described previously [10].

The C-terminal cysteine-rich domains of Dkk1/2 interact with LRP5/6 [5, 10], whose extracellular region contains four well defined YWTD (SEQ ID NO: 19) repeat domains that have a typical symmetrical six-bladed β-propeller fold [28, 29]. Although each of the first three β-propeller domains can interact with Dkk1/2, only the third is required for Dkk1/2-mediated inhibition of Wnt signaling, presumably because it binds favorably to Dkk1/2 [10]. Furthermore, the residues involved in Dkk-mediated Wnt inhibition in the third β-propeller domain of LRP5 (LRP5-PD3) were found by alanine substitution mapping [10] to be clustered on a concave, amphitheatre-shaped surface centered on the pseudo-6-fold axis atop the β-propeller [10]. This amphitheatre-shaped ligand binding site is likely to be the common feature among these β-propeller domains (FIG. 6) [30, 31]. Because of the network of hydrogen bonds within the β-propeller domains and the nature of the concave surface, the ligand binding sites of the β-propeller domains are rigid [30]. Typical ligands of these the β-propeller domains are rigid as well [30, 31]. The rigidity of the ligands and receptors minimizes loss of entropy upon binding and promotes a high affinity [30]. The rigidity also makes it possible to model the complex by docking ligands to β-propeller domains. For example, at CAPRI, different groups successfully docked laminin to the β-propeller of nidogen successfully [32, 33]. We therefore conducted a docking study to examine the interaction between Dkk2C2 and LRP5-PD3. To maximize the accuracy of this study, we used the program HADDOCK [20] to incorporate data from mutagenesis studies of the binding of Dkk1/2 to LRP5/6.

The mutation E721A on the amphitheatre surface of LRP5-PD3 that binds to Dkk had the strongest effect on Dkk1-mediated inhibition of Wnt1 activity (~70% reduction) and abolished binding of LRP5-PD3 to Dkk1 [10]. Because the corresponding residue in nidogen, Glu$^{994}$, forms a salt bridge with a lysine residue in bound laminin [30], we speculated that Glu$^{721}$ of LRP5 would form a salt bridge with a basic residue in the bound Dkk1/2. In mutagenesis studies, we substituted each positively charged amino acid in the C-terminal cysteine-rich domain of Dkk1 (including lysine, arginine, and histidine) with glutamic acid and investigated the effect on Dkk1-LRP6 binding. Among the four Dkk1 mutants, H210E, K217E, and R242E reduced the binding of Dkk1 to LRP6 by more than 50%, and H267E reduced the binding of Dkk1 to LRP6 by about 43% (FIG. 4A). We also examined the effects of these four mutants on Dkk1-mediated inhibition of Wnt3a activity and found that, indeed, these mutants attenuated Dkk1-mediated antagonism of Wnt signaling (FIG. 4B).

Example 5

Elucidation of the Complex of LRP5 Bound with Dkk

The software package ICM (Molsoft) was used to build the structures of the first three β-propeller domains of LRP5 (termed as LRP5-PD1, PRP5-PD2, and LRP5-PD3) using the crystal structure of the low density lipoprotein receptor YWTD (SEQ ID NO: 19) β-propeller domain (Protein Data Bank code 1IJQ [PDB] [18]) as the template. The initial homology model structures were refined and evaluated by using software package AMBER8 [19]. In this step, a 5-ns molecular dynamic simulation with 2 femtoseconds/step was performed by placing the individual propeller domain in a TIP3P water box.

The docking studies used the HADDOCK [20] program. First, the homology model of the third β-propeller domain of LRP5 (LRP5-PD3) and the solution structure of Dkk2C2 were used as starting structures. Mutation of the Tyr$^{719}$, Glu$^{721}$, Arg$^{764}$, Trp$^{780}$, Asp$^{887}$, and Phe$^{888}$ residues of LRP5-PD3 had an effect of >10% on Dkk-mediated inhibition of Wnt activity. These residues were defined as active residues, and the neighboring surface residues (Arg$^{652}$, Ala$^{653}$, Val$^{694}$, Lys$^{697}$, Asp$^{718}$, Gln$^{737}$, Gly$^{738}$, Asn$^{762}$, Gly$^{781}$, Pro$^{784}$, Arg$^{805}$, Trp$^{863}$, His$^{866}$, and Met$^{890}$) were defined as passive residues. In Dkk2C2, mutation of His$^{198}$ (His$^{210}$ in Dkk1), Lys$^{205}$ (Lys$^{217}$), Arg$^{230}$ (Arg$^{242}$), and His$^{254}$ (His$^{267}$) strongly disrupted both Dkk-mediated Wnt inhibition and LRP6 binding; these residues were defined as active residues. Passive residues were neighboring surface residues Glu$^{179}$, Phe$^{199}$, Trp$^{201}$, Thr$^{201}$, Leu$^{203}$, Pro$^{206}$, Glu$^{212}$, Val$^{213}$, Lys$^{216}$, Gln$^{217}$, Glu$^{226}$, Ile$^{227}$, Gln$^{229}$, Val$^{241}$, Thr$^{246}$, Ser$^{249}$, Arg$^{252}$, and Leu$^{253}$. The flexible interface was defined as active and passive residues ±2 sequential residues for the purpose of docking. Ambiguous interaction restraints used in the docking process were defined as an ambiguous distance between all active and passive residues shown to be involved at the interaction interface.

The docking calculation was initiated with two proteins separated by 150 Å with random starting orientations. Three stages of docking solutions (rigid-body docking, semi-flexible simulated annealing, and a final refinement in water) were executed sequentially by energy minimization. Complex structures were sorted according to the intermolecular interaction energy (the sum of intermolecular van der Waals and electrostatic energies and restraint energies). In the last water refinement stage, the 100 docking structures with the lowest intermolecular interaction energies were generated and clustered on the basis of a 1.0-Å backbone root mean square deviation tolerance at the binding interface. The final docking complex structure was the structure that had the lowest intermolecular interaction energy within the cluster with the lowest average intermolecular interaction energy.

On the basis of the mutagenesis studies, we first used the HADDOCK software package to build the complex structure of Dkk2C2 bound to LRP5-PD3. As mutation of the Tyr$^{719}$, Glu$^{721}$, Arg$^{761}$, Trp$^{780}$, Asp$^{887}$, and Phe$^{888}$ residues of LRP5-PD3 had an effect of >10% on Dkk-mediated inhibition of Wnt activity [10], we proposed that these residues are involved in the interaction between Dkk2C2 and LRP5-PD3. We thus defined these residues as active residues, and 14 neighboring residues (Arg$^{652}$, Ala$^{653}$, Val$^{694}$, Lys$^{697}$, Asp$^{718}$, Gln$^{737}$, Gly$^{738}$, Asn$^{762}$, Gly$^{781}$, Pro$^{784}$, Arg$^{805}$, Trp$^{863}$, His$^{866}$, and Met$^{890}$) as passive residues. Similarly, in Dkk2C2, as mutation of His$^{198}$ (His$^{210}$ in Dkk1), Lys$^{205}$ (Lys$^{217}$ in Dkk1), Arg$^{230}$ (Arg$^{242}$ in Dkk1), and His$^{254}$ (His$^{267}$ in Dkk1) strongly disrupted both Dkk-mediated inhibition and LRP6 binding, we defined these residues and 14 of their neighbor residues as active and passive residues, respectively. In the docking process, the flexible interfaces of both Dkk2C2 and LRP5-PD3 were defined as active and passive residues ±2 sequential residues and the ambiguous interaction restraints as the distances between all active and passive residues. The docking calculation was initiated with the two proteins separated by 150 Å with random starting orientations. Three stages of docking solutions (rigid-body docking, initial refinement with semi-flexible simulated annealing, and a final refinement in water) were executed sequentially by energy minimization. During the first-stage rigid-body docking, a total of 1,000 docking structures were generated, and the top 100 docking structures with the lowest intermolecular interaction energies were selected in the second and third refinement stages. After the docking, a cluster analysis was also carried out to further evaluate the final 100 structures. To our surprise, the 100 final docking structures could be clustered on the basis of a 1.0-Å backbone root mean square deviation tolerance at the binding interface between Dkk2C2 and LRP5-PD3, indicating that complex structure generated by our docking studies has very high accuracy [34].

Figure 5:
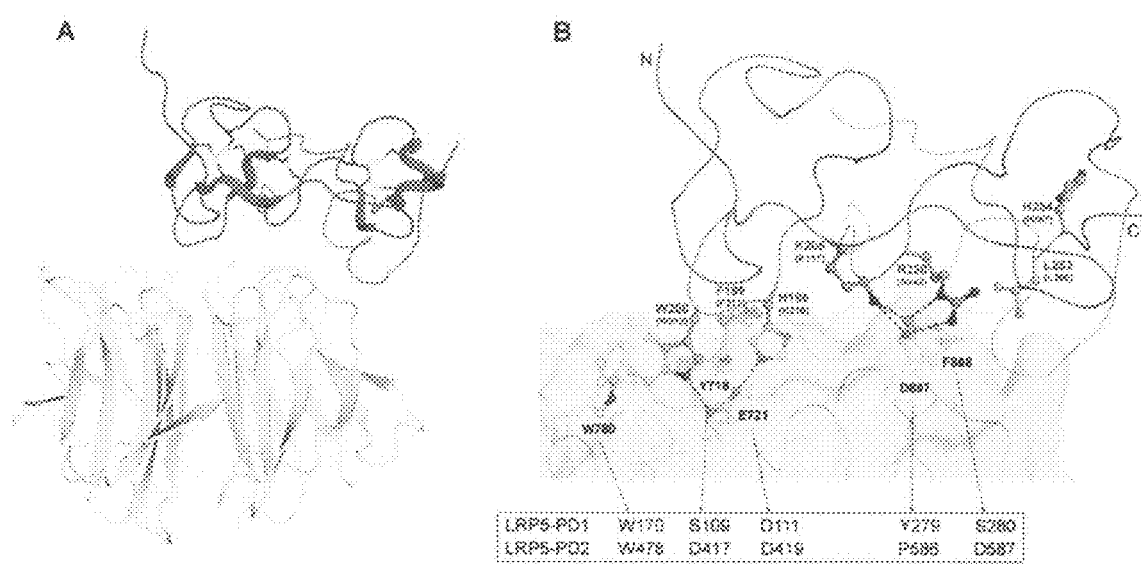
FIG. 5. Complex structure of the third β-propeller domain of LRP5 (LRP5-PD3) bound to Dkk2C2. A, a ribbon diagram of the complex of LRP5-PD3 bound to Dkk2C2. B, side chain interactions between Dkk2C2 and LRP5-PD3. Dashed lines represent hydrogen bonds. Residue numbers in brackets are the numbers in mouse Dkk1. Corresponding amino acids in LRP5-PD1 and LRP5-PD2 to those involved in LRP5-PD3 binding interface are listed in the right bottom panel. Figures were generated by using the Pymol program (DeLano Scientific).

In the complex of Dkk2C2 bound to LRP5-PD3 generated by the HADDOCK studies, the side chains of those residues at the interface form an extensive network of contacts between the two molecules, and those contacts are consistent with the mutagenesis studies reported in this study as well as in the earlier studies [10]. In particular, the second finger loop (loop β2-β3) of Dkk2C2 in the first subdomain lies atop LRP5-PD3 and the three aromatic residues, $His^{198}$ $Phe^{199}$, and $Trp^{200}$, form a "roof" that covers the amphitheatre of LRP5-PD3 (FIG. 5A). At this interface, the side chain of $His^{198}$ in Dkk2C2 ($His^{210}$ in Dkk1) forms a hydrogen bond with the side chain of $Glu^{721}$ in LRP5-PD3, and $Trp^{200}$ in Dkk2C2 ($W^{212}$ in Dkk1) also interacts with $Glu^{121}$ of LRP5-PD3 (FIG. 5B). Furthermore, there are many hydrophobic interactions between the roof and the surface of the "amphitheatre" that also significantly contribute to the binding between the two molecules; among them, the benzoic ring contacts between $Phe^{199}$ and $Trp^{200}$ in Dkk2C2 and $Tyr^{719}$ and $Trp^{780}$ in LRP5-PD3 are most visible. Another interaction hot spot between Dkk2C2 and LRP5-PD3 involves the second subdomain of Dkk2C2. In this binding site, the side chain of $Arg^{230}$ ($Arg^{242}$ in Dkk1) in Dkk2C2 forms hydrogen bonds with the side chain of $Asp^{887}$ in LRP5-PD3. In addition, the side chain $Leu^{253}$ ($Leu^{266}$ in Dkk1) in Dkk2C2 and $Phe^{888}$ in LRP5-PD3 form a hydrophobic network. Indeed, mutation of this hydrophobic residue in Dkk1, L266A, efficiently disrupted inhibition of Dkk1-mediated Wnt3a activity (about 30%; data not shown) and the binding of Dkk1 to LRP6 (about 40%; data not shown). Interestingly, although the second subdomain of Dkk2C2 has two mobile finger loops, in the complex, the residues that are involved in the interaction with LRP5-PD3 are all in a relatively rigid conformation (FIG. 3).

Figure 4:
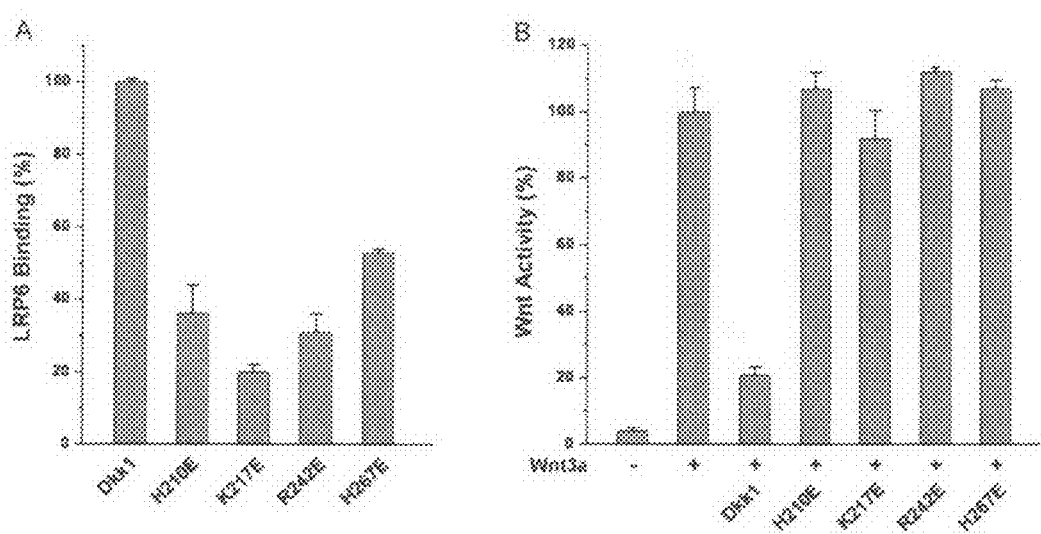
FIG. 4. Ability of Dkk1 and its mutants to bind to LRP6 and antagonize Wnt activity. A, binding of Dkk1 and its mutants to LRP6. HEK cells were transfected with the LRP6 plasmid and 1 day later were incubated on ice with conditioned medium containing wild-type and mutant mouse Dkk1-AP for 2 h. After cells were washed and lysed, the AP activities in cell lysates were determined. The activity resulted from the binding of wild-type Dkk1-AP to LRP6 was taken as 100%. B, effect of Dkk1 and its mutants on the inhibition of Wnt activity. NIH3T3 cells were transfected with a LEF-1 activity reporter plasmid and an enhanced green fluorescent protein plasmid. 24 h after transfection, cells were treated with Wnt3a conditioned medium and wild-type or mutant Dkk1 conditioned medium for 6 h. The luciferase activities in cell lysates were determined as described in the legend to FIG. 1.

Two other residues, $Lys^{205}$ ($Lys^{217}$ in Dkk1) and $His^{254}$ ($His^{267}$ in Dkk1) in Dkk2C2, also play a role in Dkk1-LRP6 binding and Dkk1-mediated inhibition of Wnt3a activity (FIG. 4). In the complex structure of Dkk2C2 bound to LRP5-PD3, $Lys^{205}$ locates at the boundary of the two binding hot spots, forming a hydrogen bond with $Asp^{887}$ of LRP5-PD3 (FIG. 5B). Interestingly, mutant K217E of Dkk1 significantly disrupted the binding of Dkk 1 to both LRP6 and another Dkk receptor Kremen protein (as described in [41]); this residue may play a role in coordinating the interactions between Dkk and its two binding partners, LRP5/6 and Kremen. On the other hand, in the structure of Dkk2C2, $His^{254}$ ($His^{267}$ in Dkk1) is buried inside the folded structure of Dkk2C2 (FIG. 5B). Therefore, the mutation H267E in Dkk1 would likely affect the overall stability of Dkk structure.

The first and second β-propeller domains of LRP5/6 also interact with Dkk1/2 but do not play an essential role in Dkk1-mediated inhibition of Wnt activity [10]. Because of the structural similarity of the YWTD (SEQ ID NO: 19) β-propeller domains, it is likely that Dkk molecules can fit into the ligand binding sites of all β-propeller domains of LRP5/6 but can fit perfectly into only that of the third β-propeller domain. Furthermore, in the complex of LRP5-PD3 bound to Dkk2C2, the residues of LRP5-PD3 at the interface are relatively conserved in the first three propeller domains of LRP5/6 (FIG. 5B). To further elucidate why the interactions of Dkk2C2 with different β-propeller domains of LRP5 lead to different effects on regulating Wnt signaling, we built the complexes of Dkk2C2 bound with LRP5-PD1 and Dkk2C2 with LRP5-PD2 by using the complex model of Dkk2C2 bound with LRP5-PD3 as the template. LRP5-PD3 in the complex template was first replaced with LRP5-PD1 and LRP5-PD2, respectively, by superimposition of the propeller domains; then the new complexes of Dkk2C2 bound with LRP5-PD1 and LRP5-PD2 were refined by the water refinement algorithm in the HADDOCK program. As expected, the Dkk2C2 fits well to the ligand binding sites of LRP5-PD1 and LRR5-PD2. Comparing the three complexes in detail, we observed that although Dkk2C2 has similar interactions with the first two β-propeller domains as it does with the third one, not all of the intermolecular interactions found in the complex of Dkk2C2 bound to the third β-propeller domain are preserved in the complexes of Dkk2C2 bound to the first two propeller domains. The most pronounced one is the amino acid Glu 72 in LRP5-PD3, which plays an important role in the interaction; this amino acid is replaced by aspartic acid in the first two propeller domains of LRP5/6 (FIG. 6). Because of the rigidity of both the ligand and receptor, the aspartic acids in the first two β-propeller domains of LRP5 are unable to interact with the bound Dkk2C2 (data not shown). Indeed, the calculated intermolecular interaction energies (mainly intermolecular van der Waals and electrostatic energies and restraint energies) between Dkk2C2 and the first two propellers were about 30% weaker than that between Dkk2C2 and LRP5-PD3 (−402.263 kcal/mol and −374.747 kcal/mol versus −558.5 kcal/mol), suggesting that Dkk2C2 binds to the first two β-propeller domains of LRP5 with lower affinities. Therefore, binding affinity is likely to be the factor that determines the selection of Dkk binding partners in the Wnt signaling pathway.

REFERENCES

1. Niehrs, C. (2006) *Oncogene* 25, 7469-7481
2. Krupnik, V. E., Sharp, J. D., Jiang, C., Robison, K., Chickering, T. W., Amaravadi, L., Brown, D. E., Guyot, D., Mays, G., Leiby, K., Chang, B., Duong, T., Goodearl, A. D., Gearing, D. P., Sokol, S. Y., and McCarthy, S. A. (1999) *Gene* 238, 301-313
3. Semenov, M. V., Tamai, K., Brott, B. K., Kuhl, M., Sokol, S., and He, X. (2001) *Curr. Biol.* 11, 951-961
4. Li, L., Mao, J. H., Sun, L., Liu, W. Z., and Wu, D. Q. (2002) *J. Biol. Chem.* 277, 5977-5981
5. Brott, B. K., and Sokol, S. Y. (2002) *Mol. Cell. Biol.* 22, 6100-6110
6. Mao, B., and Niehrs, C. (2003) *Gene* 302, 179-183
7. Bafico, A., Liu, G., Yaniv, A., Gazit, A., and Aaronson, S. A. (2001) *Nat. Cell Biol.* 3, 683-686
8. Li, Y., Lu, W., He, X., Schwartz, A. L., and Bu, G. (2004) *Oncogene* 23, 9129-9135
9. Mao, B., Wu, W., Davidson, G., Marhold, J., Li, M., Mechler, B. M., Delius, H., Hoppe, D., Stannek, P., Walter, C., Glinka, A., and Niehrs, C. (2002) *Nature* 417, 664-667
10. Zhang, Y., Wang, Y., Li, X., Zhang, J., Mao, J., Li, Z., Zheng, J., Li, L., Harris, S., and Wu, D. (2004) *Mol. Cell. Biol.* 24, 4677-4684

11. Wong, H. C., Mao, J., Nguyen, J. T., Srinivas, S., Zhang, W., Liu, B., Li, L., Wu, D., and Zheng, J. (2000) *Nat. Struct. Biol.* 7, 1178-1184
12. Li, L., Yuan, H., Xie, W., Mao, J., Caruso, A. M., McMahon, A., Sussman, D. J., and Wu, D. (1999) *J. Biol. Chem.* 274, 129-134
13. Wong, H. C., Bourdelas, A., Krauss, A., Lee, H.-J., Shao, Y.-M., Wu, D., Mlodzik, M., Shi, D. L., and Zheng, J. (2003) *Mol. Cell.* 12, 1251-1260
14. Delaglio, F., Grzesiek, S., Vuister, G. W., Zhu, G., Pfeifer, J., and Bax, A. (1995) *J. Biomol. NMR* 6, 277-293
15. Eccles, C., Guntert, P., Billeter, M., and Wuthrich, K. (1991) *J. Biomol. NMR* 1, 111-130
16. Guntert, P., Braun, W., and Wuthrich, K. (1991) *J. Mol. Biol.* 217, 517-530
17. Guntert, P., Mumenthaler, C., and Wuthrich, K. (1997) *J. Mol. Biol.* 273, 283-298
18. Jeon, H., Meng, W. Y., Takagi, J., Eck, M. J., Springer, T. A., and Blacklow, S. C. (2001) *Nat. Struct. Biol.* 8, 499-504
19. Case, D. A., Cheatham, T. E., III, Darden, T., Gohlke, H., Luo, R., Merz, K. M., Jr., Onufriev, A., Simmerling, C., Wang, B., and Woods, R. J. (2005) *J. Comput. Chem.* 26, 1668-1688
20. Dominguez, C., Boelens, R., and Bonvin, A. M. (2003) *J. Am. Chem. Soc.* 125, 1731-1737
21. Wong, H. C., Liu, G., Zhang, Y. M., Rock, C. O., and Zheng, J. (2002) *J. Biol. Chem.* 277, 15874-15880
22. Sali, A., and Overington, J. P. (1994) *Protein Sci.* 3, 1582-1596
23. Thornton, J. M. (1981) *J. Mol. Biol.* 151, 261-287
24. Holm, L., and Sander, C. (1993) *J. Mol. Biol.* 233, 123-138
25. van, T. H., Sarda, L., Verger, R., and Cambillau, C. (1992) *Nature* 359, 159-162
26. Boisbouvier, J., Albrand, J. P., Blackledge, M., Jaquinod, M., Schweitz, H., Lazdunski, M., and Marion, D. (1998) *J. Mol. Biol.* 283, 205-219
27. van, T. H., Bezzine, S., Cambillau, C., Verger, R., and Carriere, F. (1999) *Biochim. Biophys. Acta* 1441, 173-184
28. Springer, T. A. (1998) *J. Mol. Biol.* 283, 837-862
29. Springer, T. A. (2002) *Curr. Opin. Struct. Biol.* 12, 802-813
30. Takagi, J., Yang, Y., Liu, J. H., Wang, J. H., and Springer, T. A. (2003) *Nature* 424, 969-974
31. Rudenko, G., Henry, L., Henderson, K., Ichtchenko, K., Brown, M. S., Goldstein, J. L., and Deisenhofer, J. (2002) *Science* 298, 2353-2358
32. Gray, J. J. (2006) *Curr. Opin. Struct. Biol.* 16, 183-193
33. Mendez, R., Leplae, R., Lensink, M. F., and Wodak, S. J. (2005) *Proteins* 60, 150-169
34. van Dijk, A. D., Boelens, R., and Bonvin, A. M. (2005) *FEBS J.* 272, 293-312
35. Springer, T. A. (1997) *Proc. Natl. Acad. Sci. U.S.A.* 94, 65-72
36. van, D. M., van Dijk, A. D., Hsu, V., Boelens, R., and Bonvin, A. M. (2006) *Nucleic Acids Res.* 34, 3317-3325
37. Bonvin, A. M. (2006) *Curr. Opin. Struct. Biol.* 16, 194-200
38. de Vries, S. J., van Dijk, A. D., Krzeminski, M., van, D. M., Thureau, A., Hsu, V., Wassenaar, T., and Bonvin, A. M. (2007) *Proteins* 69, 726-733
39. Koradi, R., Billeter, M., and Wuthrich, K. (1996) *J. Mol. Graph.* 14, 29-32
40. Esnouf, R. M. (1997) *J. Mol. Graph. Model.* 15, 132-133
41. Wang, K., Zhang, Y., Li, X., Chen, L., Wang, H., Wu, J., Zheng, J., and Wu, D. (2008) *J. Biol. Chem.* 283, 23371-23375

What is claimed is:

1. A method for modulating Dickkopf (Dkk) activity in a cell, said method comprising a step of decreasing Dkk activity in said cell by administering to said cell a compound that disrupts the interaction of a Dkk polypeptide with an LDL receptor-related protein (LRP) polypeptide, wherein the compound is a low density lipoprotein receptor-related protein 5 or 6 (LRP5 or LRP6) third propeller domain (LRP5-PD3 or LRP6-PD3) or a modification thereof having one or more conservative substitutions, wherein said LRP5-PD3, LRP6-PD3 or modification thereof has an amino acid sequence having at least 85% identity to SEQ ID NO:4, wherein said compound does not comprise a full length LRP.

2. The method of claim 1, wherein said cell is a mammalian cell.

3. The method of claim 1, wherein said cell is a human cell.

4. The method of claim 1, wherein said cell is an osteoblast.

5. The method of claim 1, wherein said cell is a cancer cell.

6. The method of claim 1, wherein the compound comprises an amino acid sequence having at least 90% identity to or SEQ ID NO:4.

7. The method of claim 1, wherein the compound comprises an amino acid sequence having at least 95% identity to SEQ ID NO:4.

8. The method of claim 1, wherein the compound comprises an amino acid sequence having 100% identity to SEQ ID NO:4.

9. The method of claim 1, wherein the cell is in a mammal having a Wnt-related disease.

10. The method of claim 9, wherein the mammal is a human.

11. The method of claim 9, wherein the Wnt-related disease is cancer.

12. The method of claim 11, wherein the cancer is selected from the group consisting of colon cancer, breast cancer, melanoma, head and neck cancer, non-small-cell lung cancer, gastric cancer, mesothelioma, Barrett's esophagus, synovial sarcoma, cervical cancer, leukemia, prostate cancer, lung cancer, and bladder cancer.

13. The method of claim 9, wherein the Wnt-related disease is selected from the group consisting of rheumatoid arthritis, schizophrenia, Alzheimer's disease, and bone disease.

* * * * *

SEQUENCE LISTING

```
<160> NUMBER OF SEQ ID NOS: 19

<210> SEQ ID NO 1
<211> LENGTH: 88
<212> TYPE: PRT
<213> ORGANISM: Mus musculus

<400> SEQUENCE: 1

Met Pro His Ile Lys Gly His Glu Gly Asp Pro Cys Leu Arg Ser Ser
1               5                   10                  15

Asp Cys Ile Asp Gly Phe Cys Cys Ala Arg His Phe Trp Thr Lys Ile
            20                  25                  30

Cys Lys Pro Val Leu His Gln Gly Glu Val Cys Thr Lys Gln Arg Lys
        35                  40                  45

Lys Gly Ser His Gly Leu Glu Ile Phe Gln Arg Cys Asp Cys Ala Lys
    50                  55                  60

Gly Leu Ser Cys Lys Val Trp Lys Asp Ala Thr Tyr Ser Ser Lys Ala
65                  70                  75                  80

Arg Leu His Val Cys Gln Lys Ile
                85

<210> SEQ ID NO 2
<211> LENGTH: 89
<212> TYPE: PRT
<213> ORGANISM: Mus musculus

<400> SEQUENCE: 2
```

Ile Tyr His Thr Lys Gly Gln Glu Gly Ser Val Cys Leu Arg Ser Ser
1               5                   10                  15

Asp Cys Ala Ala Gly Leu Cys Cys Ala Arg His Phe Trp Ser Lys Ile
            20                  25                  30

Cys Lys Pro Val Leu Lys Glu Gly Gln Val Cys Thr Lys His Lys Arg
            35                  40                  45

Lys Gly Ser His Gly Leu Glu Ile Phe Gln Arg Cys Tyr Cys Gly Glu
50                  55                  60

Gly Leu Ala Cys Arg Ile Gln Lys Asp His His Gln Ala Ser Asn Ser
65              70                  75                  80

Ser Arg Leu His Thr Cys Gln Arg His
                85

<210> SEQ ID NO 3
<211> LENGTH: 258
<212> TYPE: PRT
<213> ORGANISM: Homo sapiens

<400> SEQUENCE: 3

Pro Glu Ala Phe Leu Val Phe Thr Ser Arg Ala Ile His Arg Ile
1               5                   10                  15

Ser Leu Glu Thr Asn Asn Asn Asp Val Ala Ile Pro Leu Thr Gly Val
            20                  25                  30

Lys Glu Ala Ser Ala Leu Asp Phe Asp Val Ser Asn Asn His Ile Tyr
            35                  40                  45

Trp Thr Asp Val Ser Leu Lys Thr Ile Ser Arg Ala Phe Met Asn Gly
50                  55                  60

Ser Ser Val Glu His Val Val Glu Phe Gly Leu Asp Tyr Pro Glu Gly
65                  70                  75                  80

Met Ala Val Asp Trp Met Gly Lys Asn Leu Tyr Trp Ala Asp Thr Gly
                85                  90                  95

Thr Asn Arg Ile Glu Val Ala Arg Leu Asp Gly Gln Phe Arg Gln Val
                100                 105                 110

Leu Val Trp Arg Asp Leu Asp Asn Pro Arg Ser Leu Ala Leu Asp Pro
                115                 120                 125

Thr Lys Gly Tyr Ile Tyr Trp Thr Glu Trp Gly Gly Lys Pro Arg Ile
            130                 135                 140

Val Arg Ala Phe Met Asp Gly Thr Asn Cys Met Thr Leu Val Asp Lys
145                 150                 155                 160

Val Gly Arg Ala Asn Asp Leu Thr Ile Asp Tyr Ala Asp Gln Arg Leu
                165                 170                 175

Tyr Trp Thr Asp Leu Asp Thr Asn Met Ile Glu Ser Ser Asn Met Leu
                180                 185                 190

Gly Gln Glu Arg Val Val Ile Ala Asp Asp Leu Pro His Pro Phe Gly
            195                 200                 205

Leu Thr Gln Tyr Ser Asp Tyr Ile Tyr Trp Thr Asp Trp Asn Leu His
            210                 215                 220

Ser Ile Glu Arg Ala Asp Lys Thr Ser Gly Arg Asn Arg Thr Leu Ile
225                 230                 235                 240

Gln Gly His Leu Asp Phe Val Met Asp Ile Leu Val Phe His Ser Ser
                245                 250                 255

Arg Gln

<210> SEQ ID NO 4
<211> LENGTH: 258

```
<212> TYPE: PRT
<213> ORGANISM: Homo sapiens

<400> SEQUENCE: 4

Pro Glu Ala Phe Leu Leu Phe Ser Arg Arg Ala Asp Ile Arg Arg Ile
1               5                   10                  15

Ser Leu Glu Thr Asn Asn Asn Val Ala Ile Pro Leu Thr Gly Val
            20                  25                  30

Lys Glu Ala Ser Ala Leu Asp Phe Asp Val Thr Asp Asn Arg Ile Tyr
        35                  40                  45

Trp Thr Asp Ile Ser Leu Lys Thr Ile Ser Arg Ala Phe Met Asn Gly
    50                  55                  60

Ser Ala Leu Glu His Val Val Glu Phe Gly Leu Asp Tyr Pro Glu Gly
65                  70                  75                  80

Met Ala Val Asp Trp Leu Gly Lys Asn Leu Tyr Trp Ala Asp Thr Gly
                85                  90                  95

Thr Asn Arg Ile Glu Val Ser Lys Leu Asp Gly Gln His Arg Gln Val
            100                 105                 110

Leu Val Trp Lys Asp Leu Asp Ser Pro Arg Ala Leu Ala Leu Asp Pro
        115                 120                 125

Ala Glu Gly Phe Met Tyr Trp Thr Glu Trp Gly Gly Lys Pro Lys Ile
    130                 135                 140

Asp Arg Ala Ala Met Asp Gly Ser Glu Arg Thr Thr Leu Val Pro Asn
145                 150                 155                 160

Val Gly Arg Ala Asn Gly Leu Thr Ile Asp Tyr Ala Lys Arg Arg Leu
                165                 170                 175

Tyr Trp Thr Asp Leu Asp Thr Asn Leu Ile Glu Ser Ser Asn Met Leu
            180                 185                 190

Gly Leu Asn Arg Glu Val Ile Ala Asp Asp Leu Pro His Pro Phe Gly
        195                 200                 205

Leu Thr Gln Tyr Gln Asp Tyr Ile Tyr Trp Thr Asp Trp Ser Arg Arg
    210                 215                 220

Ser Ile Glu Arg Ala Asn Lys Thr Ser Gly Gln Asn Arg Thr Ile Ile
225                 230                 235                 240

Gln Gly His Leu Asp Tyr Val Met Asp Ile Leu Val Phe His Ser Ser
                245                 250                 255

Arg Gln

<210> SEQ ID NO 5
<211> LENGTH: 88
<212> TYPE: PRT
<213> ORGANISM: Homo sapiens

<400> SEQUENCE: 5

Met Ser His Ile Lys Gly His Glu Gly Asp Pro Cys Leu Arg Ser Ser
1               5                   10                  15

Asp Cys Ile Glu Gly Phe Cys Cys Ala Arg His Phe Trp Thr Lys Ile
            20                  25                  30

Cys Lys Pro Val Leu His Gln Gly Glu Val Cys Thr Lys Gln Arg Lys
        35                  40                  45

Lys Gly Ser His Gly Leu Glu Ile Phe Gln Arg Cys Asp Cys Ala Lys
    50                  55                  60

Gly Leu Ser Cys Lys Val Trp Lys Asp Ala Thr Tyr Ser Ser Lys Ala
65                  70                  75                  80

Arg Leu His Val Cys Gln Lys Ile
                85
```

```
<210> SEQ ID NO 6
<211> LENGTH: 88
<212> TYPE: PRT
<213> ORGANISM: Xenopus sp.

<400> SEQUENCE: 6

Ile Pro His Ile Lys Gly His Glu Gly Asp Pro Cys Leu Arg Ser Thr
1               5                   10                  15

Asp Cys Ile Glu Gly Phe Cys Cys Ala Arg His Phe Trp Thr Lys Ile
            20                  25                  30

Cys Lys Pro Val Leu His Gln Gly Glu Val Cys Thr Lys Leu Arg Lys
        35                  40                  45

Lys Gly Ser His Gly Leu Glu Ile Phe Gln Arg Cys Asp Cys Ala Lys
    50                  55                  60

Gly Leu Ser Cys Lys Val Trp Lys Asp Ala Thr Tyr Ser Ser Lys Ser
65                  70                  75                  80

Arg Leu His Ile Cys Gln Lys Ile
                85

<210> SEQ ID NO 7
<211> LENGTH: 89
<212> TYPE: PRT
<213> ORGANISM: Homo sapiens

<400> SEQUENCE: 7

Met Tyr His Thr Lys Gly Gln Glu Gly Ser Val Cys Leu Arg Ser Ser
1               5                   10                  15

Asp Cys Ala Ser Gly Leu Cys Cys Ala Arg His Phe Trp Ser Lys Ile
            20                  25                  30

Cys Lys Pro Val Leu Lys Glu Gly Gln Val Cys Thr Lys His Arg Arg
        35                  40                  45

Lys Gly Ser His Gly Leu Glu Ile Phe Gln Arg Cys Tyr Cys Gly Glu
    50                  55                  60

Gly Leu Ser Cys Arg Ile Gln Lys Asp His His Gln Ala Ser Asn Ser
65                  70                  75                  80

Ser Arg Leu His Thr Cys Gln Arg His
                85

<210> SEQ ID NO 8
<211> LENGTH: 89
<212> TYPE: PRT
<213> ORGANISM: Unknown
<220> FEATURE:
<223> OTHER INFORMATION: Description of Unknown: Rabbit Dkk1 polypeptide

<400> SEQUENCE: 8

Met Tyr His Ala Lys Gly Gln Glu Gly Ser Val Cys Leu Arg Ser Ser
1               5                   10                  15

Asp Cys Ala Thr Gly Leu Cys Cys Ala Arg His Phe Trp Ser Lys Ile
            20                  25                  30

Cys Lys Pro Val Leu Lys Glu Gly Gln Val Cys Thr Lys His Arg Arg
        35                  40                  45

Lys Gly Ser His Gly Leu Glu Ile Phe Gln Arg Cys Tyr Cys Gly Asp
    50                  55                  60

Gly Leu Ser Cys Arg Leu Gln Asn Asp Gln His Glu Ala Ser Asn Ser
65                  70                  75                  80

Ser Arg Leu His Thr Cys Gln Arg His
                85
```

<210> SEQ ID NO 9
<211> LENGTH: 90
<212> TYPE: PRT
<213> ORGANISM: Xenopus sp.

<400> SEQUENCE: 9

```
Met Gln Pro Phe Lys Gly Arg Asp Gly Asp Val Cys Leu Arg Ser Thr
1               5                   10                  15

Asp Cys Ala Pro Gly Leu Cys Cys Ala Arg His Phe Trp Ser Lys Ile
            20                  25                  30

Cys Lys Pro Val Leu Asp Glu Gly Gln Val Cys Thr Lys His Arg Arg
        35                  40                  45

Lys Gly Ser His Gly Leu Glu Ile Phe Gln Arg Cys His Cys Gly Ala
    50                  55                  60

Gly Leu Ser Cys Arg Leu Gln Lys Gly Glu Phe Thr Thr Val Pro Lys
65                  70                  75                  80

Thr Ser Arg Leu His Thr Cys Gln Arg His
                85                  90
```

<210> SEQ ID NO 10
<211> LENGTH: 87
<212> TYPE: PRT
<213> ORGANISM: Danio rerio

<400> SEQUENCE: 10

```
Asn Gln Met Leu Lys Gly Leu Glu Gly Glu Asn Cys Leu Arg Ser Ser
1               5                   10                  15

Asp Cys Ala Glu Thr Leu Cys Cys Ala Arg His Phe Trp Ser Lys Ile
            20                  25                  30

Cys Lys Pro Val Leu Lys Glu Gly Gln Val Cys Thr Lys His Lys Arg
        35                  40                  45

Lys Gly Thr His Gly Leu Glu Ile Phe Gln Arg Cys Asp Cys Gly Glu
    50                  55                  60

Gly Leu Ser Cys Arg Thr Gln Arg Gly Asp Gly Lys Ala Ser Arg
65                  70                  75                  80

Ser Leu His Thr Cys Gln Arg
                85
```

<210> SEQ ID NO 11
<211> LENGTH: 88
<212> TYPE: PRT
<213> ORGANISM: Mus sp.

<400> SEQUENCE: 11

```
Ser Gln Ser Ser Lys Gly Gln Glu Gly Glu Ser Cys Leu Arg Thr Ser
1               5                   10                  15

Asp Cys Gly Pro Gly Leu Cys Cys Ala Arg His Phe Trp Thr Lys Ile
            20                  25                  30

Cys Lys Pro Val Leu Arg Glu Gly Gln Val Cys Ser Arg Arg Gly His
        35                  40                  45

Lys Asp Thr Ala Gln Ala Pro Glu Ile Phe Gln Arg Cys Asp Cys Gly
    50                  55                  60

Pro Gly Leu Thr Cys Arg Ser Gln Val Thr Ser Asn Arg Gln His Ser
65                  70                  75                  80

Arg Leu Arg Val Cys Gln Arg Ile
                85
```

```
<210> SEQ ID NO 12
<211> LENGTH: 91
<212> TYPE: PRT
<213> ORGANISM: Homo sapiens

<400> SEQUENCE: 12

Ser Gln Gly Arg Lys Gly Gln Glu Gly Glu Ser Cys Leu Arg Thr Phe
1               5                   10                  15

Asp Cys Gly Pro Gly Leu Cys Cys Ala Arg His Phe Trp Thr Lys Ile
            20                  25                  30

Cys Lys Pro Val Leu Leu Glu Gly Gln Val Cys Ser Arg Arg Gly His
        35                  40                  45

Lys Asp Thr Ala Gln Ala Pro Glu Ile Phe Gln Arg Cys Asp Cys Gly
    50                  55                  60

Pro Gly Leu Leu Cys Arg Ser Gln Leu Thr Ser Asn Arg Gln His Ala
65                  70                  75                  80

Arg Leu Arg Val Cys Gln Lys Ile Glu Lys Leu
                85                  90

<210> SEQ ID NO 13
<211> LENGTH: 261
<212> TYPE: PRT
<213> ORGANISM: Homo sapiens

<400> SEQUENCE: 13

Ile Ala Tyr Leu Phe Phe Thr Asn Arg His Glu Val Arg Lys Met Thr
1               5                   10                  15

Leu Asp Arg Ser Glu Tyr Thr Ser Leu Ile Pro Asn Leu Arg Asn Val
            20                  25                  30

Val Ala Leu Asp Thr Glu Val Ala Ser Asn Arg Ile Tyr Trp Ser Asp
        35                  40                  45

Leu Ser Gln Arg Met Ile Cys Ser Thr Gln Leu Asp Arg Ala His Gly
    50                  55                  60

Val Ser Ser Tyr Asp Thr Val Ile Ser Arg Asp Ile Gln Ala Pro Asp
65                  70                  75                  80

Gly Leu Ala Val Asp Trp Ile His Ser Asn Ile Tyr Trp Thr Asp Ser
                85                  90                  95

Val Leu Gly Thr Val Ser Val Ala Asp Thr Lys Gly Val Lys Arg Lys
            100                 105                 110

Thr Leu Phe Arg Glu Asn Gly Ser Lys Pro Arg Ala Ile Val Val Asp
        115                 120                 125

Pro Val His Gly Phe Met Tyr Trp Thr Asp Trp Gly Thr Pro Ala Lys
    130                 135                 140

Ile Lys Lys Gly Gly Leu Asn Gly Val Asp Ile Tyr Ser Leu Val Thr
145                 150                 155                 160

Glu Asn Ile Gln Trp Pro Asn Gly Ile Thr Leu Asp Leu Leu Ser Gly
                165                 170                 175

Arg Leu Tyr Trp Val Asp Ser Lys Leu His Ser Ile Ser Ser Ile Asp
            180                 185                 190

Val Asn Gly Gly Asn Arg Lys Thr Ile Leu Glu Asp Glu Lys Arg Leu
        195                 200                 205

Ala His Pro Phe Ser Leu Ala Val Phe Glu Asp Lys Val Phe Trp Thr
    210                 215                 220

Asp Ile Ile Asn Glu Ala Ile Phe Ser Ala Asn Arg Leu Thr Gly Ser
225                 230                 235                 240

Asp Val Asn Leu Leu Ala Glu Asn Leu Leu Ser Pro Glu Asp Met Val
                245                 250                 255
```

```
Leu Phe His Asn Leu
        260

<210> SEQ ID NO 14
<211> LENGTH: 263
<212> TYPE: PRT
<213> ORGANISM: Mus sp.

<400> SEQUENCE: 14

Gly Thr His Leu Leu Phe Ala Gln Thr Gly Lys Ile Glu Arg Leu Pro
1               5                   10                  15

Leu Glu Arg Asn Thr Met Lys Lys Thr Glu Ala Lys Ala Phe Leu His
            20                  25                  30

Ile Pro Ala Lys Val Ile Ile Gly Leu Ala Phe Asp Cys Val Asp Lys
        35                  40                  45

Val Val Tyr Trp Thr Asp Ile Ser Glu Pro Ser Ile Gly Arg Ala Ser
    50                  55                  60

Leu His Gly Gly Glu Pro Thr Thr Ile Ile Arg Gln Asp Leu Gly Ser
65                  70                  75                  80

Pro Glu Gly Ile Ala Leu Asp His Leu Gly Arg Thr Ile Phe Trp Thr
                85                  90                  95

Asp Ser Gln Leu Asp Arg Ile Glu Val Ala Lys Met Asp Gly Thr Gln
            100                 105                 110

Arg Arg Val Leu Phe Asp Thr Gly Leu Val Asn Pro Arg Gly Ile Val
        115                 120                 125

Thr Asp Pro Val Arg Gly Asn Leu Tyr Trp Thr Asp Trp Asn Arg Asp
    130                 135                 140

Asn Pro Lys Ile Glu Thr Ser His Met Asp Gly Thr Asn Arg Arg Ile
145                 150                 155                 160

Leu Ala Gln Asp Asn Leu Gly Leu Pro Asn Gly Leu Thr Phe Asp Ala
                165                 170                 175

Phe Ser Ser Gln Leu Cys Trp Val Asp Ala Gly Thr His Arg Ala Glu
            180                 185                 190

Cys Leu Asn Pro Ala Gln Pro Gly Arg Arg Lys Val Leu Glu Gly Leu
        195                 200                 205

Gln Tyr Pro Phe Ala Val Thr Ser Tyr Gly Lys Asn Leu Tyr Tyr Thr
    210                 215                 220

Asp Trp Lys Thr Asn Ser Val Ile Ala Met Asp Leu Ala Ile Ser Lys
225                 230                 235                 240

Glu Met Asp Thr Phe His Pro His Lys Gln Thr Arg Leu Tyr Gly Ile
                245                 250                 255

Thr Ile Ala Leu Ser Gln Cys
        260

<210> SEQ ID NO 15
<211> LENGTH: 260
<212> TYPE: PRT
<213> ORGANISM: Homo sapiens

<400> SEQUENCE: 15

Ala Glu Glu Val Leu Leu Leu Ala Arg Arg Thr Asp Leu Arg Arg Ile
1               5                   10                  15

Ser Leu Asp Thr Pro Asp Phe Thr Asp Ile Val Leu Gln Val Asp Asp
            20                  25                  30

Ile Arg His Ala Ile Ala Ile Asp Tyr Asp Pro Leu Glu Gly Tyr Val
        35                  40                  45
```

-continued

```
Tyr Trp Thr Asp Asp Glu Val Arg Ala Ile Arg Arg Ala Tyr Leu Asp
         50                  55                  60

Gly Ser Gly Ala Gln Thr Leu Val Asn Thr Glu Ile Asn Asp Pro Asp
65                  70                  75                  80

Gly Ile Ala Val Asp Trp Val Ala Arg Asn Leu Tyr Trp Thr Asp Thr
                 85                  90                  95

Gly Thr Asp Arg Ile Glu Val Thr Arg Leu Asn Gly Thr Ser Arg Lys
                100                 105                 110

Ile Leu Val Ser Glu Asp Leu Asp Glu Pro Arg Ala Ile Ala Leu His
            115                 120                 125

Pro Val Met Gly Leu Met Tyr Trp Thr Asp Trp Gly Glu Asn Pro Lys
130                 135                 140

Ile Glu Cys Ala Asn Leu Asp Gly Gln Glu Arg Arg Val Leu Val Asn
145                 150                 155                 160

Ala Ser Leu Gly Trp Pro Asn Gly Leu Ala Leu Asp Leu Gln Glu Gly
                165                 170                 175

Lys Leu Tyr Trp Gly Asp Ala Lys Thr Asp Lys Ile Glu Val Ile Asn
                180                 185                 190

Val Asp Gly Thr Lys Arg Arg Thr Leu Leu Glu Asp Lys Leu Pro His
            195                 200                 205

Ile Phe Gly Phe Thr Leu Leu Gly Asp Phe Ile Tyr Trp Thr Asp Trp
210                 215                 220

Gln Arg Arg Ser Ile Glu Arg Val His Lys Val Lys Ala Ser Arg Asp
225                 230                 235                 240

Val Ile Ile Asp Gln Leu Pro Asp Leu Met Gly Leu Lys Ala Val Asn
                245                 250                 255

Val Ala Lys Val
            260

<210> SEQ ID NO 16
<211> LENGTH: 260
<212> TYPE: PRT
<213> ORGANISM: Homo sapiens

<400> SEQUENCE: 16

Ala Thr Glu Leu Leu Leu Ala Arg Arg Thr Asp Leu Arg Arg Ile
1               5                   10                  15

Ser Leu Asp Thr Pro Asp Phe Thr Asp Ile Val Leu Gln Leu Glu Asp
                20                  25                  30

Ile Arg His Ala Ile Ala Ile Asp Tyr Asp Pro Val Glu Gly Tyr Ile
            35                  40                  45

Tyr Trp Thr Asp Asp Glu Val Arg Ala Ile Arg Arg Ser Phe Ile Asp
         50                  55                  60

Gly Ser Gly Ser Gln Phe Val Val Thr Ala Gln Ile Ala His Pro Asp
65                  70                  75                  80

Gly Ile Ala Val Asp Trp Val Ala Arg Asn Leu Tyr Trp Thr Asp Thr
                 85                  90                  95

Gly Thr Asp Arg Ile Glu Val Thr Arg Leu Asn Gly Thr Met Arg Lys
                100                 105                 110

Ile Leu Ile Ser Glu Asp Leu Glu Glu Pro Arg Ala Ile Val Leu Asp
            115                 120                 125

Pro Met Val Gly Tyr Met Tyr Trp Thr Asp Trp Gly Glu Ile Pro Lys
130                 135                 140

Ile Glu Arg Ala Ala Leu Asp Gly Ser Asp Arg Val Val Leu Val Asn
145                 150                 155                 160
```

```
Thr Ser Leu Gly Trp Pro Asn Gly Leu Ala Leu Asp Tyr Asp Glu Gly
            165                 170                 175
Lys Ile Tyr Trp Gly Asp Ala Lys Thr Asp Lys Ile Glu Val Met Asn
            180                 185                 190
Thr Asp Gly Thr Gly Arg Arg Val Leu Val Glu Asp Lys Ile Pro His
            195                 200                 205
Ile Phe Gly Phe Thr Leu Leu Gly Asp Tyr Val Tyr Trp Thr Asp Trp
            210                 215                 220
Gln Arg Arg Ser Ile Glu Arg Val His Lys Arg Ser Ala Glu Arg Glu
225                 230                 235                 240
Val Ile Ile Asp Gln Leu Pro Asp Leu Met Gly Leu Lys Ala Thr Asn
            245                 250                 255
Val His Arg Val
            260

<210> SEQ ID NO 17
<211> LENGTH: 262
<212> TYPE: PRT
<213> ORGANISM: Homo sapiens

<400> SEQUENCE: 17

Ala Ser Pro Leu Leu Leu Phe Ala Asn Arg Arg Asp Val Arg Leu Val
1               5                   10                  15
Asp Ala Gly Gly Val Lys Leu Glu Ser Thr Ile Val Val Ser Gly Leu
            20                  25                  30
Glu Asp Ala Ala Ala Val Asp Phe Gln Phe Ser Lys Gly Ala Val Tyr
            35                  40                  45
Trp Thr Asp Val Ser Glu Glu Ala Ile Lys Gln Thr Tyr Leu Asn Gln
    50                  55                  60
Thr Gly Ala Ala Val Gln Asn Val Val Ile Ser Gly Leu Val Ser Pro
65                  70                  75                  80
Asp Gly Leu Ala Cys Asp Trp Val Gly Lys Lys Leu Tyr Trp Thr Asp
                85                  90                  95
Ser Glu Thr Asn Arg Ile Glu Val Ala Asn Leu Asn Gly Thr Ser Arg
            100                 105                 110
Lys Val Leu Phe Trp Gln Asp Leu Asp Gln Pro Arg Ala Ile Ala Leu
            115                 120                 125
Asp Pro Ala His Gly Tyr Met Tyr Trp Thr Asp Trp Gly Glu Thr Pro
            130                 135                 140
Arg Ile Glu Arg Ala Gly Met Asp Gly Ser Thr Arg Lys Ile Ile Val
145                 150                 155                 160
Asp Ser Asp Ile Tyr Trp Pro Asn Gly Leu Thr Ile Asp Leu Glu Glu
                165                 170                 175
Gln Lys Leu Tyr Trp Ala Asp Ala Lys Leu Ser Phe Ile His Arg Ala
            180                 185                 190
Asn Leu Asp Gly Ser Phe Arg Gln Lys Val Val Glu Gly Ser Leu Thr
            195                 200                 205
His Pro Phe Ala Leu Thr Leu Ser Gly Asp Thr Leu Tyr Trp Thr Asp
            210                 215                 220
Trp Gln Thr Arg Ser Ile His Ala Cys Asn Lys Arg Thr Gly Gly Lys
225                 230                 235                 240
Arg Lys Glu Ile Leu Ser Ala Leu Tyr Ser Pro Met Asp Ile Gln Val
                245                 250                 255
Leu Ser Gln Glu Arg Gln
            260
```

```
<210> SEQ ID NO 18
<211> LENGTH: 261
<212> TYPE: PRT
<213> ORGANISM: Homo sapiens

<400> SEQUENCE: 18

Ala Ala Pro Leu Leu Leu Tyr Ala Asn Arg Arg Asp Leu Arg Leu Val
1               5                   10                  15

Asp Ala Thr Asn Gly Lys Glu Asn Ala Thr Ile Val Val Gly Gly Leu
            20                  25                  30

Glu Asp Ala Ala Ala Val Asp Phe Val Phe Ser His Gly Leu Ile Tyr
        35                  40                  45

Trp Ser Asp Val Ser Glu Glu Ala Ile Lys Arg Thr Glu Phe Asn Lys
50                  55                  60

Thr Glu Ser Val Gln Asn Val Val Val Ser Gly Leu Leu Ser Pro Asp
65                  70                  75                  80

Gly Leu Ala Cys Asp Trp Leu Gly Glu Lys Leu Tyr Trp Thr Asp Ser
                85                  90                  95

Glu Thr Asn Arg Ile Glu Val Ser Asn Leu Asp Gly Ser Leu Arg Lys
            100                 105                 110

Val Leu Phe Trp Gln Glu Leu Asp Gln Pro Arg Ala Ile Ala Leu Asp
        115                 120                 125

Pro Ser Ser Gly Phe Met Tyr Trp Thr Asp Trp Gly Glu Val Pro Lys
130                 135                 140

Ile Glu Arg Ala Gly Met Asp Gly Ser Ser Arg Phe Ile Ile Ile Asn
145                 150                 155                 160

Ser Glu Ile Tyr Trp Pro Asn Gly Leu Thr Leu Asp Tyr Glu Glu Gln
                165                 170                 175

Lys Leu Tyr Trp Ala Asp Ala Lys Leu Asn Phe Ile His Lys Ser Asn
            180                 185                 190

Leu Asp Gly Thr Asn Arg Gln Ala Val Val Lys Gly Ser Leu Pro His
        195                 200                 205

Pro Phe Ala Leu Thr Leu Phe Glu Asp Ile Leu Tyr Trp Thr Asp Trp
210                 215                 220

Ser Thr His Ser Ile Leu Ala Cys Asn Lys Tyr Thr Gly Glu Gly Leu
225                 230                 235                 240

Arg Glu Ile His Ser Asp Ile Phe Ser Pro Met Asp Ile His Ala Phe
                245                 250                 255

Ser Gln Gln Arg Gln
            260

<210> SEQ ID NO 19
<211> LENGTH: 4
<212> TYPE: PRT
<213> ORGANISM: Unknown
<220> FEATURE:
<223> OTHER INFORMATION: Description of Unknown: Beta-propeller domain
      peptide

<400> SEQUENCE: 19

Tyr Trp Thr Asp
1
```